(12) United States Patent
Ludevid Mugica et al.

(10) Patent No.: US 7,575,898 B2
(45) Date of Patent: Aug. 18, 2009

(54) PRODUCTION OF PEPTIDES AND PROTEINS BY ACCUMULATION IN PLANT ENDOPLASMIC RETICULUM-DERIVED PROTEIN BODIES

(75) Inventors: Maria Dolores Ludevid Mugica, Barcelona (ES); Margarita Torrent Quetglas, Barcelona (ES); Sabine Ramassamy, Barcelona (ES)

(73) Assignee: ERA Plantech, S.L., Barcelona (ES)

( * ) Notice: Subject to any disclaimer, the term of this patent is extended or adjusted under 35 U.S.C. 154(b) by 487 days.

(21) Appl. No.: 10/213,462

(22) Filed: Aug. 6, 2002

(65) Prior Publication Data

US 2004/0005660 A1 Jan. 8, 2004

(30) Foreign Application Priority Data

Jun. 28, 2002 (ES) ................ 200201508

(51) Int. Cl.
*C12N 15/82* (2006.01)
(52) U.S. Cl. .............. 435/69.7; 435/320.1; 435/468; 536/23.4; 800/278
(58) Field of Classification Search ............. 435/320.1; 536/23.4
See application file for complete search history.

(56) References Cited

U.S. PATENT DOCUMENTS

| | | | |
|---|---|---|---|
| 4,215,040 | A | 7/1980 | Hager |
| 5,948,682 | A | 9/1999 | Moloney et al. |
| 6,642,437 | B1 | 11/2003 | Lemaux et al. |
| 2005/0244924 | A1 | 11/2005 | Wagner et al. |

FOREIGN PATENT DOCUMENTS

| | | |
|---|---|---|
| WO | WO 96/21029 | 7/1996 |
| WO | WO 00/40738 | 7/2000 |
| WO | WO 02/086077 | 10/2002 |

OTHER PUBLICATIONS

Ofoghi H. et al. Cloning and expression of human calcitonin genes in transgenic potato plants. Biotechnology Letters, vol. 22, No. 7, Apr. 2000, pp. 611-615.*
McKee C. et al. Production of biologically active salmon calcitonin in the milk of transgenic rabbits. Nat Biotechnol. Jul. 1998;16(7):647-51.*
Torrent M. et al. Lysine-rich modified gamma-zeins accumulate in protein bodies of transiently transformed maize endosperms. Plant Mol Biol. May 1997;34(1):139-49.*
Geli M.I. et al. Two Structural Domains Mediate Two Sequential Events in gamma-Zein Targeting: Protein Endoplasmic Reticulum Retention and Protein Body Formation. Plant Cell. Dec. 1994;6(12):1911-1922.*
Cramer C.L. et al. Transgenic plants for therapeutic proteins: linking upstream and downstream strategies. Curr Top Microbiol Immunol. 1999;240:95-118. Review.*
Conrad U. et al. Compartment-specific accumulation of recombinant immunoglobulins in plant cells: an essential tool for antibody production and immunomodulation of physiological functions and pathogen activity. Plant Mol Biol. Sep. 1998;38(1-2):101-9. Review.*
Reichel C. et al. Enhanced green fluorescence by the expression of an Aequorea victoria green fluorescent protein mutant in mono- and dicotyledonous plant cells. Proc Natl Acad Sci U S A. Jun. 11, 1996;93(12):5888-93.*
Ludevid Mugica et al., Sequence 7, Publication No. US20040005660A1, Jan. 8, 2004.*
Bevan, M. 1984, *Nucleic Acids Research* 12:8711-8721.
Conrad, U. and Fiedler, U. 1998, *Plant Mol. Biol.* 38:101-109.
Dilsen et al., 2000, *Appl. Microbiol. Biotechnol.* 54:361-369.
Düring et al., 1990, *Plant Mol. Biol.* 15:281-293.
Fischer, R. and Emans, N. 2000, *Transgenic Research* 9:279-299.
Haq et al., 1995, *Science* 268:714-715.
Herman, E.M. and Larkins, B.A. 1999, *Plant Cell* 11:601-613.
Hong et al., 2000, *Biochem. Biophys. Res.Com.* 267:362-367.
Kogan et al., 2001, *J. Mol. Biol.* 00:1-7.
Logemann et al., 1987, *Anal. Biochem.* 163:16-20.
Ludevid et al., 1984, *Plant Mol. Biol.* 3:277-234.
Ma et al., 1998, *Nat. Med.* 4:601-606.
Ma, J.K. and Hein, M.B. 1995, *Plant Physiol.* 109:341-346.
McCormick et al., 1999, *Proc. Natl. Aca. Sci. USA* 96 (2):703-708.
McKee et al., 1998, *Nature Biotechnology* 16:647-651.
Merli et al., 1996, *Protein Express. Purif.* 7:347-354.

(Continued)

*Primary Examiner*—Cynthia Collins
(74) *Attorney, Agent, or Firm*—Husch Blackwell Sanders Welsh & Katz

(57) ABSTRACT

A nucleic acid molecule is disclosed as containing a first nucleic acid sequence comprising a nucleotide sequence that encodes γ-zein protein, or a fragment thereof capable of directing and retaining a protein towards the endoplasmic reticulum (ER) of a plant cell; a second nucleic acid sequence containing a nucleotide sequence that encodes an amino acid sequence that is specifically cleavable by enzymatic or chemical means; and a third nucleic acid sequence containing the nucleotide sequence that encodes a peptide or protein of interest. Methods of using this nucleic acid molecule for transforming host plant cells and producing the peptide or protein of interest are also disclosed.

21 Claims, 13 Drawing Sheets

OTHER PUBLICATIONS

Moore et al., 1991, *J. Cell Biol.* 112:589-602.
Munro, S. and Pelham, H.R.B. 1987, *Cell* 48:899-907.
Müntz, K. 1998, *Plant Mol. Biol.* 38:77-99.
Parmenter et al., 1995, *Plant Mol. Biol.* 29:1167-1180.
Ray et al., 1993, *Bio/Technology* 11:64-70.
Reichel et al., 1996, *Proc. Natl. Acad. Sci. USA* 93:5888-5893.
Staub et al., 2000, *Nature Biotechnology* 18:333-338.
Stöger et al., 2000, *Plant Mol. Biol.* 42:583-590.
Takahashi et al., 19997, *Peptides* 18:439-444.
Torrent et al., 1986, Plant Mol. Biol. 7:393-403.
Torres et al., 1999, *Transgenic Research* 8:441-449.
Verch et al., 1999, *J. Immunol. Methods* 220:69-75.
Vitale, A. and Denecke, J. 1999, *Plant Cell* 11:615-628.
Wandelt et al., 1992, *Plant J.* 2:181-192.
Yamamoto et al., 2001, *EMBO J.* 20(12):3082-3091.
Cudd et al., 1995, *J. Pharm. Sci.* 84:717-719.
Eipper et al., 1992, *Annu. Rev. Neurosci.* 15:57-85.
Vitale et al., 1993, *J. Exp. Bot.*44:1417-1444.
Torrent et al., 1994, *Planta* 192:512-518.
Azria et al., 1995 *Tissue Int.* 57(6):405-408.
Cramer et al., 1999 *Curr. Top. Microbiol. Immunol.* 240:95-118.
Reginster, J.Y. 1993 *Am. J. Med.* 95(5A):44S-47S.
Silverman, S.L. 1997 *Am. J. Med. Sci.* 313(1):13-16.
Yabuta et al., 1995 *Appl. Microbiol. Biotechnol.* 42(5):703-708.
Geli et al., 1994, *Plant Cell* 6:1911-1922.
Ems-McClung et al., 2002 *Plant Science* 162(1):131-141.
Alvarez et al., 1998 *Planta (Berlin)* 205(3):420-427.
Philip et al., 1998 *Plant Science* 137(2):191-204.
Torrent et al., 1997 *Plant Molecular Biology* Geli et al., 1994, *Plant Cell* 6:1911-1922 (34(1):139-149.
Goytia, E. et al., "Production of Plum Pox Virus HC-Pro Functionally Active for Aphid Transmission in a Transient-Expression System", *Journ. of General Virol.*, 37:3413-3423 (2006).
Shukla et al., "Zein: The Industrial Protein from Corn", *Industrial Crops and Product*, 13:171-192 (2001).
International Search Reports dated Mar. 21, 2006.
International Search Reports dated Apr. 21, 2006.
International Search Reports dated Nov. 23, 2007.
International PCT Invitation with Annex Search Reports dated Jul. 31, 2007.
Altschuler et al., "The N- and C-Terminal Regions Regulate the Transport of Wheat γ-Gliadin through the Endoplasmic Reticulum in Xenopus Oocytes," *The Plant Cell*, 5:443-450 (Apr. 1993).
Cameron-Mills, "The Structure and Composition of Protein Bodies Purified from Barley Endosperm by Silica Sol Density Gradients", *Carlsberg Res. Commun*, 45:557-576 (1980).
Kim et al., "Zein Protein Interactions, Rather Than the Asymmetric Distribution of Zein mRNAs on Endoplasmic Reticulum Membranes, Influence Protein Body Formation in Maize Endosperm," *The Plant Cell*, 14:655-672, Mar. 2002.
Mainieri et al., "Zeolin. A New Recombinant Storage Protein Constructed Using Maize γ-Zein and Bean Phaseolin," *Plant Physiol.*, 136:3447-3456 (2004).
Miflin, et al., "The Development of Protein Bodies in the Storage Tissues of Seeds: Subcellular Separations of Homogenates of Barley, Maize, and Wheat Endosperms and of Pea Cotyledons," *Journ. of Exp. Botany*, 32:199-219 (1981).
Richard et al., "Transport and Deposition of Cereal Prolamins", *Plant Physiol. Biochem.*, 34:237-243 (1996).
Rosenberg et al., "Wheat (Wheat (*Triticum aestivum* L.) γ-Gliadin Accumulates in Dense Proteins Bodies within the Endoplasmic Reticulum of Yeast," *Plant Physiol.*, 102:61-69 (1993).
Sojikul et al., "A Plant Signal Peptide-Hepatitis B Surface Antigen Fusion Protein with Enhanced Stability and Immunogenicity Expressed in Plant Cells," PNAS, 100(5):2209-2214 (2003).
Takagi et al., "A Rice-Based Edible Vaccine Expressing Multiple T Cell Epitopes Induces Oral Tolerance for Inhibition of Th2-Mediated 1gE Responses," *PNAS*, 102(48):17525-17530 (2005).
Wallace et al., "Aggregation of Lysine-Containing Zeins into Protein Bodies in *Xenopus Oocytes*," *Science*, 240:662-664 (1988).

* cited by examiner

SEQ ID NO: 1

```
atgagggtgttgctcgttgccctcgctctcctggctctcgctgcgagcgccacctccacg
 M  R  V  L  L  V  A  L  A  L  L  A  L  A  A  S  A  T  S  T
catacaagcggcggctgcggctgccagccaccgccgccggttcatctaccgccgccgtg
 H  T  S  G  G  C  G  C  Q  P  P  P  P  V  H  L  P  P  P  V
catctgccacctccggttcacctgccacctccggtgcatctcccaccgccggtccacctg
 H  L  P  P  P  V  H  L  P  P  P  V  H  L  P  P  P  V  H  L
ccgccgccggtccacctgccaccgccggtccatgtgccgccgccggttcatctgccgccg
 P  P  P  V  H  L  P  P  P  V  H  V  P  P  P  V  H  L  P  P
ccaccatgccactaccctactcaaccgccccggcctcagcctcatccccagccacaccca
 P  P  C  H  Y  P  T  Q  P  P  R  P  Q  P  H  P  Q  P  H  P
tgcccgtgccaacagccgcatccaagcccgtgccagctgcagggaacctgcggcgttggc
 C  P  C  Q  Q  P  H  P  S  P  C  Q  L  Q  G  T  C  G  V  G
agcacccgatcctgggccagtgcgtcgagtttctgaggcatcagtgcagcccgacggcg
 S  T  P  I  L  G  Q  C  V  E  F  L  R  H  Q  C  S  P  T  A
acgccctactgctcgcctcagtgccagtcgttgcggcagcagtgttgccagcagctcagg
 T  P  Y  C  S  P  Q  C  Q  S  L  R  Q  Q  C  C  Q  Q  L  R
caggtggagccgcagcaccggtaccaggcgatcttcggcttggtcctccagtccatcctg
 Q  V  E  P  Q  H  R  Y  Q  A  I  F  G  L  V  L  Q  S  I  L
cagcagcagccgcaaagcggccaggtcgcggggctgttggcggcgcagatagcgcagcaa
 Q  Q  Q  P  Q  S  G  Q  V  A  G  L  L  A  A  Q  I  A  Q  Q
ctgacggcgatgtgcggcctgcagcagccgactccatgcccctacgctgctgccggcggt
 L  T  A  M  C  G  L  Q  Q  P  T  P  C  P  Y  A  A  A  G  G
gtcccccacgcc
 V  P  H  A
```

—— Signal peptide
— · Repeat domain
▪▪▪▪▪ Pro-X domain

FIG. 1A

SEQ ID NO: 3 atgagggtgttgctcgttgccctcgctctcctggctctcgctgcgagcgccacctccacg
M R V L L V A L A L L A L A A S A T S T catacaagcggcggctgcggctgccagccaccgccgccggttcatctaccgccgccggtg
H T S G G C G C Q P P P P V H L P P P V catctgccacctccggttcacctgccacctccggtgcatctcccaccgccggtccacctg
H L P P P V H L P P P V H L P P P V H L ccgccgccggtccacctgccaccgccggtccatgtgccgccgccggttcatctgccgccg
P P P V H L P P P V H V P P P V H L P P ccaccatgccactaccctactcaaccgccccggcctcagcctcatccccagccacaccca
P P C H Y P T Q P P R P Q P H P Q P H P tgcccgtgccaacagccgcatccaagcccgtgccagacc
C P C Q Q P H P S P C Q T

SEQ ID NO: 5 atgagggtgttgctcgttgccctcgctctcctggctctcgctgcgagcgccacctccacg
M R V L L V A L A L L A L A A S A T S T catacaagcggcggctgcggctgccagccaccgccgccggttcatctaccgccgccggtg
H T S G G C G C Q P P P P V H L P P P V catctgccacctccggttcacctgccacctccggtgcatctcccaccgccggtccacctg
H L P P P V H L P P P V H L P P P V H L ccgccgccggtccacctgccaccgccggtccatgtgccgccgccggttcatctgccgccg
P P P V H L P P P V H V P P P V H L P P ccaccatgccactaccctactcaaccgccccggacc
P P C H Y P T Q P P R T —— Signal peptide
— · Repeat domain
····· Pro-X domain

FIG. 1B

SEQ ID NO: 7 atgagggtgttgctcgttgccctcgctctcctggctctcgctgcgagcgccacctccacg
M   R   V   L   L   V   A   L   A   L   L   A   L   A   A   S   A   T   S   T
catacaagcggcggctgcggctgccagccaccgccgccggttcatctgccgccgccacca
H   T   S   G   G   C   G   C   Q   P   P   P   P   V   H   L   P   P   P   P
tgccactaccctacacaaccgccccggcctcagcctcatccccagccacacccatgcccg
C   H   Y   P   T   Q   P   P   R   P   Q   P   H   P   Q   P   H   P   C   P
tgccaacagccgcatccaagcccgtgccagacc
C   Q   Q   P   H   P   S   P   C   Q   T

SEQ ID NO: 9 atgagggtgttgctcgttgccctcgctctcctggctctcgctgcgagcgccacctccacg
M   R   V   L   L   V   A   L   A   L   L   A   L   A   A   S   A   T   S   T
catacaagcggcggctgcggctgccaatgccactaccctactcaaccgccccggcctcag
H   T   S   G   G   C   G   C   Q   C   H   Y   P   T   Q   P   P   R   P   Q
cctcatccccagccacacccatgcccgtgccaacagccgcatccaagcccgtgccagacc
P   H   P   Q   P   H   P   C   P   C   Q   Q   P   H   P   S   P   C   Q   T ——— Signal peptide
━━ ▪ Repeat domain
▪▪▪▪▪ Pro-X domain

FIG. 1C

```
                          EK              CT
                   ┌───────────────┬──────────────→
1  NT    D    D    D    D    K  │ C    S    N    L    S    T    C
2  5'       GAC  GAC  GAC  GAC  AAG  TGC  TCC  AAC  CTC  TCT  ACC  TGC
3  5'                                 TGC  TCC  AAT  CTC  TCT  ACT  TGC

1  V    L    G    K    L    S    Q    E    L    H    K    L    Q    T
2  GTT  CTT  GGT  AAG  CTC  TCT  CAG  GAG  CTT  CAC  AAG  CTC  CAG  ACT
3  GTT  CTG  GGG  AAG  TTG  AGT  CAG  GAA  TTA  CAT  AAG  CTG  CAA  ACT

1  Y    P    R    T    N    T    G    S    G    T    P    G    ter
2  TAC  CCT  AGA  ACC  AAC  ACT  GGT  TCC  GGT  ACA  CCT  GGT  TGA   3'
3  TAC  CCG  CGT  ACC  AAC  ACT  GGT  TCT  TCT  ACC  ACA              3'
```

FIG. 2

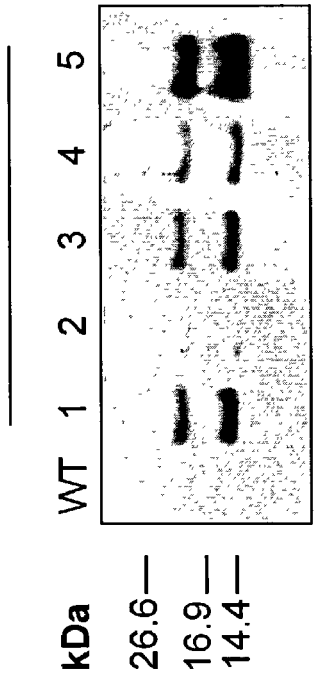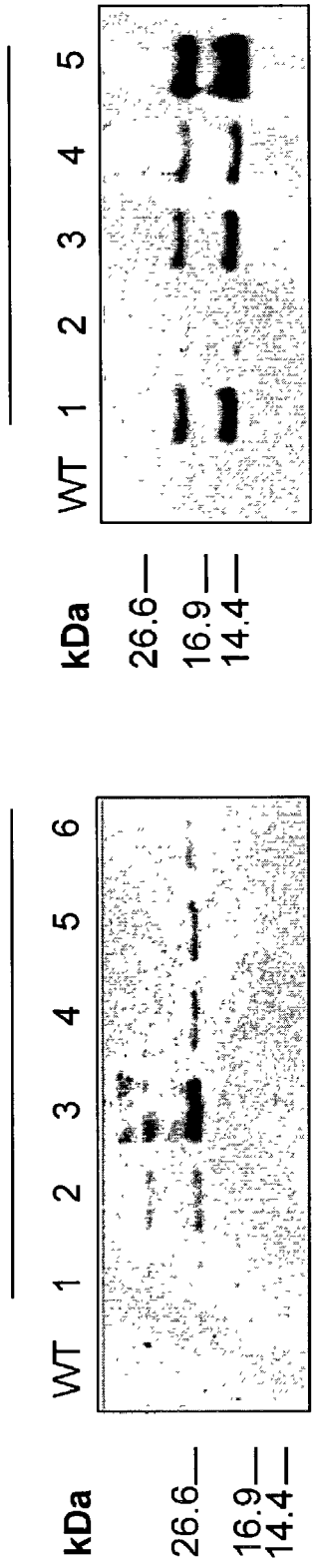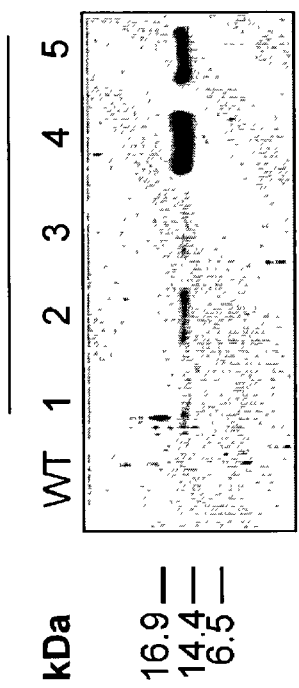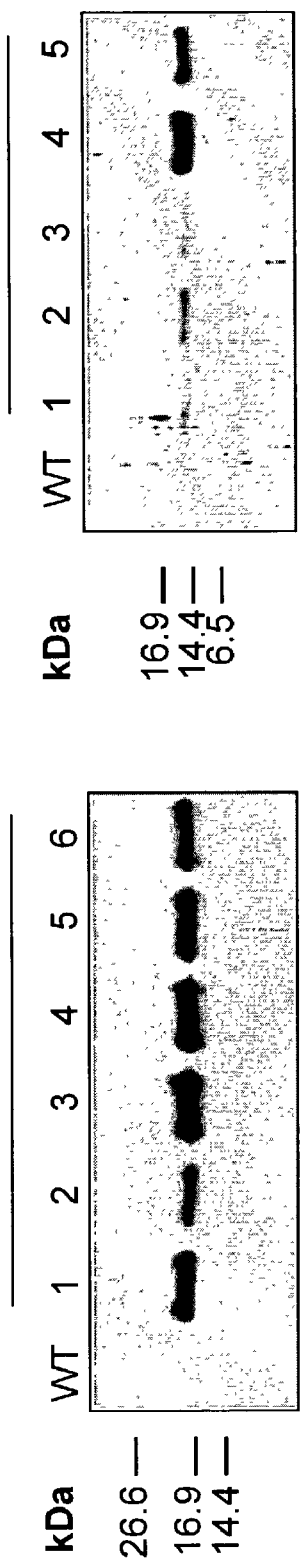
FIG. 6

PRODUCTION OF PEPTIDES AND PROTEINS BY ACCUMULATION IN PLANT ENDOPLASMIC RETICULUM-DERIVED PROTEIN BODIES

FIELD OF THE INVENTION

The present invention relates to the production of peptides and proteins of interest in host system plants by accumulation thereof in endoplasmic reticulum-derived protein bodies. The present invention also relates to nucleic acid molecules encoding such products and to the use of said nucleic acid molecules in the manufacture of constructs and vectors for transforming host plant systems.

DESCRIPTION OF THE RELATED ART

As the demand for biopharmaceuticals is expected to increase considerably because of the remarkable advances in genome knowledge and in related biomedical research, there is a considerable interest in elaborating low cost recombinant production systems.

Genetic engineering of plants to produce biopharmaceuticals is relatively recent since other transgenic systems including bacteria, fungi and cultured mammalian cells, have been largely and for a long time adopted for bio-production. Nevertheless, some recombinant therapeutic proteins using plant expression system are already on the market or in various stages of human clinical trials like hirudin, an anticoagulant protein to treat thrombosis (Parmenter et al., Plant Mol. Biol. 29:1167-1180, 1995), a chimeric IgG—IgA vaccine against dental caries (Ma et al., Nat. Med. 4:601-606, 1998), a bacterial vaccinogen against an enterotoxigenic strain of E. coli (Haq et al., Science 268:714-715, 1995), and a recombinant dog gastric lipase to treat cystic fibrosis (Bénicourt et al., Clinical Ecology of Cystic Fibrosis, pp. 291-295, H. Escobar et al. (eds), Elsevier Sciences Publishers BV, Amsterdam, 1993).

Plant expression systems are attractive because expression level of recombinant proteins can be enhanced by exploiting the innate sorting and targeting mechanisms that plants use to target host proteins to organelles. Moreover plant-derived biopharmaceuticals can be easily scale up for mass production and have the advantage to minimize health risks arising from contamination with pathogens or toxins.

Plants, more and more, appear to be an attractive expression system because of their potential to provide unlimited quantities of biologically active material at low production costs and with reduced health risks. The capacity of plants to accumulate high levels of recombinant proteins and to perform most of post-translational modifications make them considered as bio-reactors for molecular farming of recombinant therapeutics (for review see Fischer et al., Transgenic Research 9:279-299, 2000). However, important decisions concerning crop species selection, tissues choice, expression and recovery strategies and post-translational processing are determinants for the feasibility of plant-based production toward commercialization (Cramer et al., Curr. Top. Microbiol. Immunol. 240:95-118, 1999).

Subcellular targeting of recombinant proteins is an important consideration for high level accumulation and correct assembly and folding of such proteins in plants. Compartmentalization of host proteins into intracellular storage organelles is generally achieved using appropriate signal peptides or whole protein fusions. A variety of recombinant therapeutic proteins have been addressed to the following compartments of plants: apoplastic space (McCormick et al., Proc. Natl. Acad. Sci. USA 96(2):703-708, 1999); chloroplasts (Staub et al., Nature Biotechnology 18:333-338, 2000); and endoplasmic reticulum (ER) (Stoger et al., Plant Mol. Biol. 42:583-590, 2000). Immunoglobulins directed to the ER compartment in transgenic plants have been shown to give 10-100 fold higher yields than when addressed to others compartments such as the apoplasm or the cytosol (Conrad et al., Plant Mol. Biol. 38:101-109, 1998).

The targeting of complex proteins such as antibodies in the ER compartment is particularly interesting because most of the post-translational modifications required to obtain a functional product take place inside the ER (Düring et al., Plant Mol. Biol. 15:281-293, 1990; Ma and Hein, Plant Physiol. 109:341-346, 1995; Conrad et al., Plant Mol. Biol. 38:101-109, 1998). Indeed, within the ER, the signal peptide is cleaved and stress proteins such as the binding IgG protein (BiP) and enzymes such as protein disulphide isomerase (PDI), function as chaperones, bind to the unassembled protein and direct subsequent folding and assembly. In addition to these particular characteristics, available evidence indicates that plant ER is highly flexible making it an ideal reservoir for heterologous pharmaceutical proteins. The ER, even if it appears to be the gateway to the secretory pathway, is also able to store proteins for short or long periods of time. Plants store amino acids for long periods in form of specific storage proteins. One mechanism to protect these storage proteins against uncontrolled premature degradation is to deposit them into ER-derived storage organelles called protein bodies (PB) (for review, Muntz, Plant Mol. Biol. 38:77-99, 1998). The assembly of such organelles as the simple accumulation of recombinant proteins into the ER lumen requires as a first step the retention of the host protein. Secretory proteins when correctly folded and assembled into the ER have a variety of cellular destinations mostly by progression via the Golgi apparatus. However, ER retention of soluble transport-competent proteins can be induced by the carboxy-terminal retention/retrieval signal KDEL (or HDEL) (Munro et al., Cell 48:899-907, 1987; Wandelt et al., Plant J. 2:181-192, 1992; Vitale et al., J. Exp. Bot. 44:1417-1444, 1993). This conserved C-terminal motif, recognized in the Golgi apparatus through transmembrane receptors, permits the recycling of escaped ER resident proteins back to the ER (Vitale et al., Plant Cell 11:615-628, 1999; Yamamoto et al., EMBO J. 20 (12):3082-3091, 2001). Many recombinant antibody fragments have been extended with the KDEL signal in order to be stably accumulated in plants ER (Verch et al., J. Immunol. Methods 220:69-75, 1998; Torres et al., Transgenic Research 8:441-449, 1999). An alternate way to generate retention and accumulation of recombinant proteins into the ER compartment is to create an appropriate fusion with a natural ER resident such as a seed storage protein.

WO 01/75312 discloses a method for producing a cytokine in a plant host system wherein said plant host system has been transformed with a chimeric nucleic acid sequence encoding said cytokine, said chimeric nucleic acid sequence comprising a first nucleic acid sequence capable of regulating the transcription in said plant host system of a second nucleic acid sequence wherein said second nucleic acid sequence encodes a signal sequence that is linked in reading frame to a third nucleic acid sequence encoding a cytokine and a fourth nucleic acid sequence linked in reading frame to the 3' end of said third nucleic acid sequence encoding a "KDEL" amino acid sequence.

Zeins are a group of proteins that are synthesized during endosperm development in corn and may be separated in four groups α, β, γ and δ, based on their solubility. Zeins can aggregate into PB directly in the ER. Plants or plant tissues comprising rumin stable protein bodies expressed as fusion proteins comprising a full-length zein protein and an operably linked proteinaceous material have been disclosed (WO 00/40738).

γ-Zein, a maize storage protein, is one of the four maize prolamins and represents 10-15% of the total protein in the maize endosperm. As other cereal prolamins, a and gramma-zeins are biosynthesized in membrane-bound polysomes at the cytoplasmic side of the rough ER, assembled within the lumen and then sequestrated into ER-derived PB (Herman et al., Plant Cell 11:601-613, 1999, Ludevid et al., Plant Mol. Biol. 3:277-234, 1984, Torrent et al., Plant Mol. Biol. 7:93-403, 1986). γ-Zein is composed of four characteristic domains i) a peptide signal of 19 amino acids, ii) the repeat domain (53 aa) containing eight units of the hexapeptide PPPVHL (SEQ ID NO: 17), iii) the prox domain where proline residues alternate with other amino acids (29 aa) and iv) the hydrophobic cysteine rich C-terminal domain (111 aa). The ability of γ-zein to assemble in ER-derived PBs is not restricted to seeds. In fact, when γ-zein gene was constitutively expressed in transgenic Arabidopsis plants, the storage protein accumulated within ER-derived PBs in leaf mesophyl cells (Geli et al, Plant Cell6:1911-1922, 1994). Looking for a signal responsible for the γ-zein deposition into the ER-derived PB (prolamins do not have KDEL signal), it has been demonstrated that the proline-rich N-terminal domain including the tandem repeat domain was necessary for ER retention and that the C-terminal domain was involved in PB formation. However, the mechanisms by which these domains promote the PB assembly are still unknown.

Calcitonin (CT), a 32-amino acid hormonal peptide is essential for correct calcium metabolism and has found widespread clinical use in the treatment of osteoporosis, hypercalcemic shock and Paget's disease (Reginster et al., Am. J. Med. 95(5A):44S-47S, 1993; Azria et al., Calcif. Tissue Int. 57(6): 405-408, 1995; Silverman et al., Am. J. Med. Sci. 313(1):13-16, 1997). Human CT is synthesized as a preproprotein with a signal peptide of 25 amino acids and two propeptides at the N- and C-terminus (57 aa and 21 aa respectively). The resultant active peptide is 32 amino acids long with a single disulphide bridge ($Cys_1$-$Cys_7$) and is amidated at the carboxy terminus. In vitro, human CT aggregates which limits its usefulness as a therapeutic. Consequently, salmon CT which is less prone to aggregate is commonly used instead (Cudd et al., J. Pharm. Sci. 84:717-719, 1995). Production of CT is currently achieved by chemical synthesis but the cost of this production encouraged some research groups to explore alternative approaches. Human and salmon CT have been produced in *E. coli* (Ray et al., Bio/Technology 11:64-70, 1993; Hong et al., Biophys. Res. Com. 267:362-367, 2000), in mouse pituitary cells (Merli et al., Purif. 7:347-354, 1996), in nonendocrine cell lines Cos-7 and CHO (Takahashi et al., Peptides 18:439-444, 1997) and more recently in the milk of transgenic rabbits (McKee et al., Nature Biotechnology 16:647-651, 1998). Production of bioactive calcitonin by biotechnological methods requires at least two processing steps: i) generation of a glycine-extended calcitonin (Bradbury et al., Bohemoslov. 37:267-274, 1988) and ii) formation of a carboxy-terminal prolinamide via the action of the amidation enzyme, peptidyl glycine a-amidating monooxygenase (PAM) (Eipper et al., Annu. Rev. Neurosci. 15: 57-85, 1992). Since it is not currently known whether the carboxyl-amidation occurs in plant cells, in vitro amidation of plant glycine-extended calcitonin with the PAM enzyme would provide the C-terminal amide (Ray et al., Bio/Technology 11:64-70, 1993).

SUMMARY OF THE INVENTION

The problem to be solved by the present invention is to provide an alternate system for producing peptides and proteins of interest in a plant host system.

The solution presented herein is based on the ability of proline rich domains of γ-zein to self-assemble and to confer stability to fusion proteins in the ER of a host plant system. The use of a γ-zein fusion protein based-system to accumulate a product of interest in a host system plant constitutes a successful approach to accumulate said product of interest within ER-derived PBs of plants.

The invention is illustrated in the Example, wherein a fusion protein based-system to accumulate recombinant CT in ER-derived PBs in tobacco plants is described. Various proline rich domains were engineered from γ-zein to serve as fusion partners through a cleavable protease site. Mature calcitonin coding region was fused at the C-terminus of the γ-zein domains and expressed in transgenic tobacco plants. The fusion proteins were accumulated in ER-derived PBs in tobacco leaves. After purification, the fusion proteins were submitted to enterokinase cleavage permitting the release of calcitonin.

Accordingly, the present invention provides a nucleic acid molecule comprising: (a) a first nucleic acid sequence comprising a nucleotide sequence that encodes γ-zein protein, or a fragment thereof capable of directing and retaining a protein towards the endoplasmic reticulum (ER) of a plant cell; (b) a second nucleic acid sequence containing a nucleotide sequence that encodes an amino acid sequence that is specifically cleavable by enzymatic or chemical means; and (c) a third nucleic acid sequence containing the nucleotide sequence that encodes a peptide or protein of interest, wherein the 3' end of said first nucleic acid sequence is linked to the 5' end of said second nucleic acid sequence and the 3' end of said second nucleic acid sequence is linked to the 5' end of said third nucleic acid sequence, wherein said nucleotide sequences are operatively linked among them.

The present invention also provides a nucleic acid construct comprising said nucleic acid molecule.

The present invention further provides a vector containing said molecule or construct and to a cell transformed with said vector.

The present invention also provides a transformed plant host system having said nucleic acid molecule, construct or vector.

The present invention further provides a transgenic plant host system comprising, said nucleic acid molecule integrated in its genome.

The present invention also provides a method for producing a peptide or protein of interest in said plant host system.

The present invention further provides a method for producing calcitonin in said plant host system.

The present invention also provides a fusion protein, said fusion protein having an amino acid sequence encoded by the above mentioned nucleic acid molecule.

BRIEF DESCRIPTION OF DRAWINGS

FIG. 1 shows the nucleotide sequences and translations of γ-zein (FIG. 1A) and γ-zein derivatives RX3 (FIG. 1B, upper), R3 (FIG. 1B, lower), P4 (FIG. 1C, upper) and X10 (FIG. 1C, lower).

FIG. 2 shows the nucleotide sequence (lane 2; SEQ ID NO: 18) and translation (lane 1; SEQ ID NO: 19) of synthetic calcitonin (CT). The synthetic CT gene was constructed using preferential plant codon usage. Codon modifications are underlined in comparison to the wild type salmon CT gene (lane 3; SEQ ID NO: 20). The synthetic gene contains at 5' end a linker sequence corresponding to the enterokinase cleavage site (EK) and is extended at 3' to produce a single C-terminal glycine.

FIG. 6 shows the results of an immunoblot analysis of the fusion proteins in transgenic tobacco plants using γ-zein antiserum. Soluble proteins were extracted from wild type (WT) and transgenic tobacco (To) leaves, separated on 15% SDS-polyacrylamide gels (20 mg per lane) and transferred to nitrocellulose. Numbers represent the independent transgenic lines obtained for the different chimeric genes, γ-zein-CT, RX3-CT, R3-CT, P4-CT.

FIG. 7B shows comparative northern blot analysis of the different chimeric gene transcripts. Total RNAs were isolated from the transgenic lines analyzed by immunoblot (FIG. 7A), fractionated on denaturing formamide gel electrophoresis (30 mg per lane) and capillary blotted onto nylon membrane. Blots were hybridized with a random primed probe (129 bases) obtained from calcitonin cDNA.

FIG. 8A shows the immunolocalization of RX3-CT protein in RX3-CT transgenic lines using CT antiserum (dilution 1:100). FIG. 8B shows the immunolocalization of P4-CT protein in P4-CT transgenic lines using CT antiserum (dilution 1:100). FIG. 8C shows the immunolocalization of RX3-CT protein in RX3-CT transgenic lines using γ-zein antiserum (dilution 1:1.500). FIG. 8D shows the immunolocalization of BiP protein in RX3-CT transgenic lines using BiP antiserum (dilution 1:250). FIG. 8E shows the immunolocalization in wild type plants using γ-zein antiserum (dilution 1:1.500). FIG. 8F shows the immunolocalization in RX3-CT transgenic plants without primary antibody (dilution 1:1.500). Immunocytochemistry on tobacco leaf sections was performed by using the primary antibodies indicated and protein A-colloidal gold (15 nm). The abbreviations are: cw=cell wall; ch=chloroplast; pb=protein body; and v=vacuole.

DETAILED DESCRIPTION OF THE INVENTION

Figure 3:
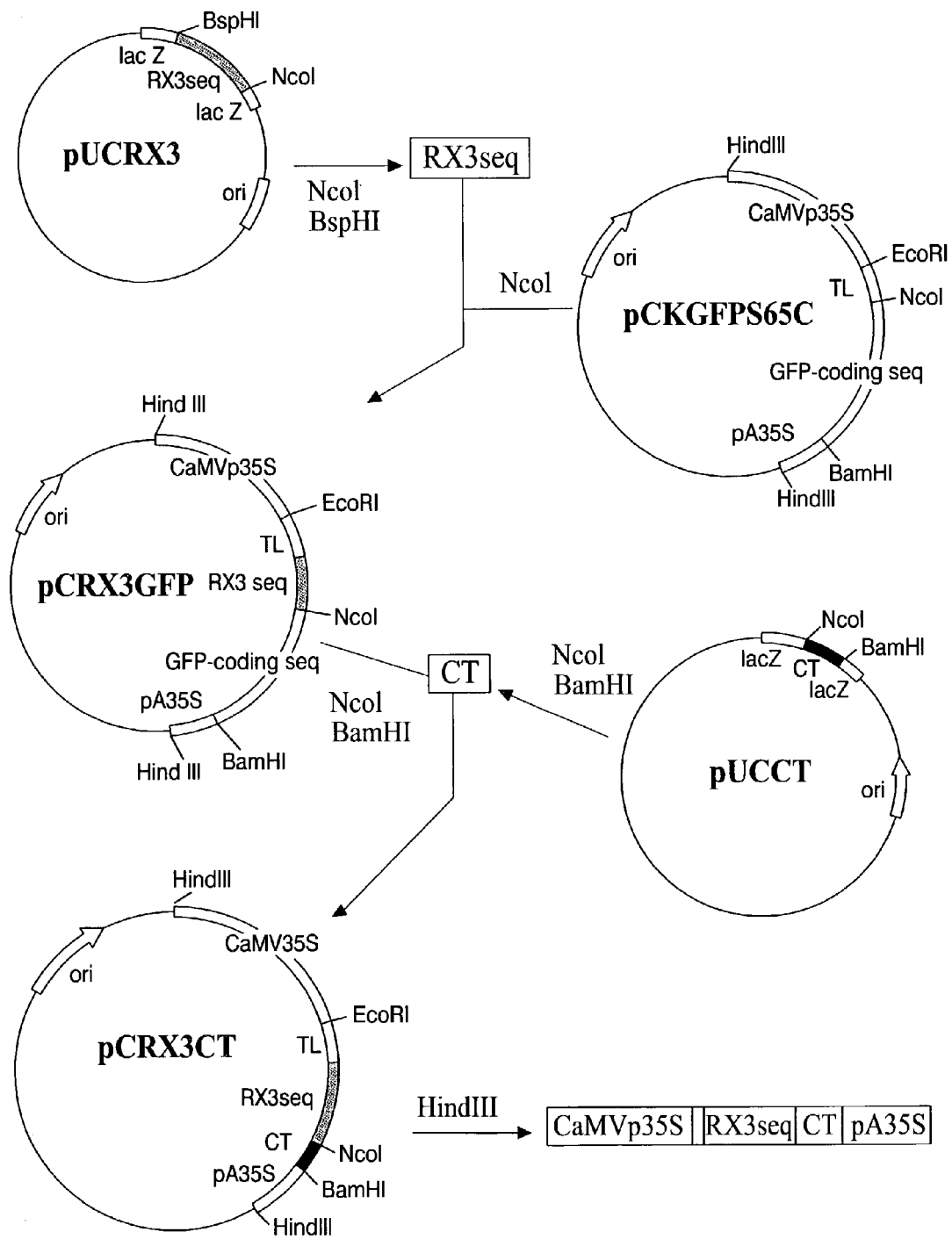
FIG. 3 shows a schematic outline for the construction of pCRX3CT plasmid. The process represented was the same for the obtention of the following plasmids pCZeinCT, pCR3CT pCP4CT and pCX10CT, the difference among them being the corresponding γ-zein or γ-zein derived sequences introduced. The different plasmids are not depicted in proportion.

The invention provides a nucleic acid molecule or sequence, hereinafter referred to as the nucleic acid sequence or molecule of the invention, comprising:(a) a first nucleic acid sequence comprising a nucleotide sequence that encodes γ-zein protein, or a fragment thereof capable of directing and retaining a protein towards the endoplasmic reticulum (ER) of a plant cell; (b) a second nucleic acid sequence containing a nucleotide sequence that encodes an amino acid sequence that is specifically cleavable by enzymatic or chemical means; and (c) a third nucleic acid sequence containing the nucleotide sequence that encodes a peptide or protein of interest, wherein the 3' end of said first nucleic acid sequence is linked to the 5' end of said second nucleic acid sequence and the 3' end of said second nucleic acid sequence is linked to the 5' end of said third nucleic acid sequence.

The term "γ-zein" as used herein refers to a maize storage protein which is composed of the four characteristic domains mentioned previously. Said term includes native γ-zein proteins, as well as variants thereof and recombinant γ-zein proteins which are capable of directing and retaining a protein towards the ER.

Preferably, the first nucleic acid sequence contains the nucleotide sequence encoding the full-length γ-zein protein. In a particular embodiment, the nucleotide sequence encoding a full-length γ-zein protein is shown in FIG. 1A and identified in SEQ ID NO: 1.

Also preferably, the first nucleic acid sequence comprises a nucleotide sequence encoding a fragment of γ-zein protein, said fragment containing a nucleotide sequence that encodes an amino acid sequence capable of directing and retaining a protein towards the ER. In this case, the first nucleic acid sequence may contain as a way of non-limiting examples:

one or more nucleotide sequences encoding all or part of the repetition domain of the protein γ-zein;

one or more nucleotide sequences encoding all or part of the ProX domain of the protein γ-zein; or one or more nucleotide sequences encoding all or part of the repetition domain of the protein γ-zein, and a nucleotide sequence that encodes all or part of the ProX domain of the protein γ-zein.

Also preferably, the first nucleic acid sequence may comprise a nucleotide sequence encoding a fragment of γ-zein protein, wherein said fragment comprises a nucleotide sequence that encodes an amino acid sequence capable of directing and retaining a protein towards the ER and is selected from the group consisting of:

the nucleotide sequence shown in SEQ ID NO: 3 [nucleotide sequence identified as RX3 (FIG. 1B)],
the nucleotide sequence shown in SEQ ID NO: 5] [nucleotide sequence identified as R3 (FIG. 1B)],
the nucleotide sequence shown in SEQ ID NO: 7 [nucleotide sequence identified as P4 (FIG. 1C)], and
the nucleotide sequence shown in SEQ ID NO: 9 [nucleotide sequence identified as X10 (FIG. 1C)].

The second nucleic acid sequence comprises a nucleotide sequence that encodes an amino acid sequence that is specifically cleavable by enzymatic or chemical means. In a particular embodiment, said second nucleic acid sequence comprises a nucleotide sequence that encodes a protease cleavage site, for example, an amino acid cleavable site by a protease such as an enterokinase, Arg—C endoprotease, Glu—C endoprotease, Lys—C endoprotease, factor Xa and the like. Alternatively, the second nucleic acid sequence comprises a nucleotide sequence that encodes an amino acid that is specifically cleavable by a chemical reagent, such as, for example, cyanogen bromide which cleaves methionine residues, or any other suitable chemical reagent.

The second nucleic acid sequence may be generated as a result of the union between said first nucleic acid sequence and said third nucleic acid sequence. In that case, each sequence contains a number of nucleotides in such a way that when said first and third nucleic acid sequences become linked a functional nucleotide sequence that encodes an amino acid sequence that is specifically cleavable by enzymatic or chemical means, i.e., the second nucleic acid sequence, is formed. In an alternate embodiment, the second nucleic acid sequence is a foreign sequence operatively inserted between said first and third nucleic acid sequence.

The third nucleic acid sequence contains the nucleotide sequence that encodes a product (a peptide or protein) of interest. In principle, any product of interest may be expressed by the system provided by the instant invention. Preferably, the product of interest is a proteinaceous (i.e., a protein or peptide) drug, for example, a peptide hormone, such as calcitonin, erythropoietin, thrombopoietin, growth hormone and the like, an interferon, i.e., a protein produced in response to viral infections and as cytokine during an immune response, etc. Also preferably, said therapeutic products of interest are effective for treating the human or animal body.

More preferably, the third nucleic acid sequence comprises a nucleotide sequence encoding calcitonin (CT), for example, human calcitonin (hCT) or salmon calcitonin (sCT). Most preferably, said third nucleic acid sequence includes a codon for glycine at the 3' end of said nucleic acid sequence encoding calcitonin thus rendering a glycine-extended calcitonin.

According to the invention, the 3' end of said first nucleic acid sequence is linked to the 5' end of said second nucleic acid sequence and the 3' end of said second nucleic acid sequence is linked to the 5' end of said third nucleic acid sequence, i.e., said first, second and third nucleic acid sequences are in reading frame.

The nucleic acid sequence of the invention may be obtained by using conventional techniques known for the skilled person in the art. In general, said techniques involve linking different fragments of the nucleic acid sequence of the invention in a suitable vector. A review of said conventional techniques may be found, for example, in "Molecular cloning, a Laboratory Manual", 2nd ed., by Sambrook et al., Cold Spring Harbor Laboratory Press, 1989. The construction of some vectors containing a nucleic acid of the invention is disclosed in the Example and illustrated in FIGS. 3 and 4. As shown therein, various proline rich domains were engineered from γ-zein to serve as fusion partners through a cleavable protease site. Mature calcitonin coding region (32 aa) was fused at the C-terminus of the γ-zein domains and expressed in transgenic tobacco plants. The fusion proteins were accumulated in ER-derived protein bodies in tobacco leaves. After purification, the fusion proteins were submitted to enterokinase cleavage permitting the release of calcitonin which may be further purified from digestion mixture by a reverse phase chromatography.

In another aspect, the invention provides a fusion protein, hereinafter referred to as the fusion protein of the invention, comprising: (i) the amino acid sequence of γ-zein protein, or a fragment thereof capable of directing and retaining a protein towards the ER of a plant cell; (ii) an amino acid sequence that is specifically cleavable by enzymatic or chemical means, and (iii) a peptide or protein of interest. Preferably, the amino acid sequence capable of directing and retaining a protein towards the ER of a plant cell is γ-zein protein, or a fragment thereof.

The fusion protein of the invention is accumulated in stable, ER-derived PBs, in a host plant system. The enzymatically or chemically cleavable site, which is present at the C-terminus of γ-zein domains, allows to recover the product of interest afterwards. The product of interest may be then isolated and purified by conventional means. Therefore, the fusion protein of the invention constitutes a novel and successful approach to accumulate a product of interest.

Preferably, the fusion protein of the invention comprises a full-length γ-zein protein. A specific amino acid sequence of full-length γ-zein is shown in FIG. 1A and identified in SEQ ID NO: 2.

Also preferably, the fusion protein of the invention comprises a fragment of a γ-zein protein, said fragment containing an amino acid sequence capable of directing and retaining a protein towards the ER. More preferably, the fusion protein of the invention comprises a fragment of a γ-zein protein and is selected from the group consisting of:

the amino acid sequence shown in SEQ ID NO: 4 [amino acid sequence corresponding to RX3 (FIG. 1B)],
the amino acid sequence shown in SEQ ID NO: 6 [amino acid sequence corresponding to R3 (FIG. 1B)],
the amino acid sequence shown in SEQ ID NO: 8 [amino acid sequence corresponding to P4 (FIG. 1C)], and
the amino acid sequence shown in SEQ ID NO: 10 [amino acid sequence corresponding to X10 (FIG. 1C)].

The fusion protein of the invention comprises an amino acid sequence that is specifically cleavable by enzymatic or chemical means. Preferably, said cleavable site comprises a protease cleavage site, for example, an amino acid cleavable site by a protease such as an enterokinase, Arg—C endoprotease, Glu—C endoprotease, Lys—C endoprotease, factor Xa and the like, or an amino acid cleavable site by a chemical reagent, such as, for example, cyanogen bromide which cleaves methionine residues, or any other suitable chemical reagent.

The fusion protein of the invention also comprises a product of interest, for example, a proteinaceous (i.e., a protein or peptide) drug, such as a peptide hormone, an interferon, and the like. Preferably, said product of interest is effective for treating the human or animal body. More preferably, the fusion protein of the invention comprises a calcitonin (CT), for example, an optionally glycine-extended human calcitonin (hCT) or salmon calcitonin (sCT).

The present invention further provides a nucleic acid construct comprising (i) the nucleic acid molecule of the invention, and (ii) a regulatory nucleotide sequence that regulates the transcription of the nucleic acid of the invention (i), said regulatory sequence (ii) being functional in plants. Said nucleic acid molecule and regulatory sequence are operatively linked.

Practically any plant functional regulatory sequence may be used. Preferably, said regulatory sequence (ii) is tissue-specific, i.e., it can regulate the transcription of the nucleic acid of the invention in a specific tissue, such as seeds, leaves, tubercles, etc.

The regulatory sequence (ii) may comprise a promoter functional in plants. Virtually, any promoter functional in plant may be used. Preferably, said regulatory sequence (ii) comprises the promoter 35SCaMV. Also preferably, said regulatory sequence (ii) comprises the "patatina" promoter, a storage protein promoter, the ubiquitine gene promoter, the regulatory sequences of the γ-zein gene, or the like.

The regulatory sequence (ii) may also comprise a transcription termination sequence. Virtually, any transcription termination sequence functional in plant may be used. Preferably, said transcription termination sequence comprises the terminator 35SCaMV, the terminator of the octopine synthase (ocs) gene, the terminator of the nopaline synthase (nos) gene, the terminator of the γ-zein gene, or the like.

The regulatory sequence (ii) may also contain a translation enhancer functional in plant. Virtually, any translation enhancer functional in plant may be used, for example, the promoting sequence for transcription of the tomato etch virus, and the like.

The nucleic acid molecule of the invention, or the construct provided by this invention, can be inserted into an appropriate vector. Therefore, the invention also provides a vector comprising the nucleic acid molecule or construct of the invention. Suitable vectors include plasmids, cosmids and viral vectors. Preferably, said vector is suitable for transforming plants. The choice of the vector may depend on the host cell wherein it is to be subsequently introduced. By way of example, the vector wherein the nucleic acid sequence of the invention is introduced may be a plasmid, a cosmid or a viral vector that, when introduced into a host cell, is integrated into the genome of said host cell and is replicated along with the chromosome (or chromosomes) in which it has been integrated. To obtain said vector, conventional methods can be used (Sambrook et al., Molecular cloning: A laboratory manual, Cold Spring Harbor, N.Y., 1989).

The invention also provides a plant host system, said plant host system having been transformed with the nucleic acid molecule of the invention, or with a construct or a vector provided by the instant invention.

As used herein, the term "plant host system" includes plants, including, but not limited to, monocots, dicots, and, specifically, cereals (e.g., maize, rice, oat, etc.), legumes (e.g., soy, etc.), cruciferous (e.g., Arabidopsis thaliana, colza, etc.) or solanaceous (e.g., potato, tomato, tobacco, etc.). A plant host system also encompasses plant cells. Plant cells include suspension cultures, embryos, merstematic regions, callus tissue, leaves, roots, shoots, gametophytes, sporophytes, pollen, seeds and microspores. A plant host system may be at various stages of maturity and may be grown in liquid or solid culture, or in soil or suitable medium in pots, greenhouses or fields. Expression in plant host systems may be transient or permanent. Plant host system also refers to any clone of such plant, seed, selfed or hybrid progeny, propagule whether generated sexually or asexually, and descendants of any of these, such as cuttings or seeds.

The transformation of plant host systems may be carried out by using conventional methods. A review of the genetic transfer to plants may be seen in the textbook entitled "Ingeniería genética and transferencia génica", by Marta Izquierdo, Ed. Pirámide (1999), in particular, Chapter 9, "Transferencia genica a plantas", pages 283-316.

The present invention also provides a transgenic plant host system, engineered to contain a novel, laboratory designed transgene, said transgenic plant host system comprising, integrated in its genome, the nucleic acid of the invention. Said transgenic plant host system may be obtained by means of conventional techniques, for example, through the use of conventional antisense mRNA techniques and/or overexpression (in sense silencing) or others, for example, by using binary vectors or other vectors available for the different plant transformation techniques currently in use. Examples of transgenic plant host systems provided by the present invention include both monocotyledon and dicotyledonous plants, and, specifically, cereals, legumes, cruciferous, solanaceous, etc.

The nucleic acid molecule of the present invention is useful for producing a product of interest in a plant host system. Therefore, the present invention further provides a method for producing a product of interest in a plant host system, which comprises growing a transformed or transgenic plant host system provided by the instant invention, under conditions that allow the production and expression of said product of interest in the form of a fusion protein. As mentioned above, said fusion protein is accumulated in stable, ER-derived PBs, in said host plant system. The enzymatically or chemically cleavable site, which is present at the C-terminus of γ-zein domains, allows to recover the product of interest afterwards. The product of interest may be then isolated and purified by conventional means. Accordingly, the method provided by the instant invention further comprises, if desired, the isolation and purification of said fusion protein, and, optionally, the release of said product of interest from said fusion protein. The fusion protein is cleaved at the cleavage site by a suitable enzyme or chemical reagent, as appropriate.

The present invention further provides a method for producing calcitonin in a plant host system, comprising:

a) transforming a plant host system with an expression vector or with a nucleic acid construct comprising a regulatory sequence for the transcription of a nucleic acid molecule that comprises:

(i) a first nucleic acid sequence comprising a nucleotide sequence that encodes γ-zein protein, or a fragment thereof capable of directing and retaining a protein towards the endoplasmic reticulum (ER) of a plant cell, (ii) a second nucleic acid sequence containing a nucleotide sequence that encodes an amino acid sequence that is specifically cleavable by enzymatic or chemical means, and (iii) a third nucleic acid sequence containing the nucleotide sequence that encodes calcitonin, wherein the 3' end of said first nucleic acid sequence is linked to the 5' end of said second nucleic acid sequence and the 3' end of said second nucleic acid sequence is linked to the 5' end of said third nucleic acid sequence;

b) generating complete plants from said plant host systems transformed with said expression vector or nucleic acid construct;

c) growing such transformed plants under conditions that allow the production and expression of calcitonin in the form of a fusion protein; and optionally d) isolating, purifying said fusion protein and treating said fusion protein in order to release calcitonin.

The invention provides, therefore, a fusion protein based system to accumulate recombinant products of interest in ER-derived PBs in plant host systems. The invention is further illustrated by the following non limitative example.

EXAMPLE 1

Production of Calcitonin in Tobacco Plants

A successful example of CT production in tobacco plants is described below. Various proline rich domains were engineered from γ-zein to serve as fusion partners through a cleavable protease site. Mature CT coding region (32 aa) was fused at the C-terminus of the γ-zein domains and expressed in transgenic tobacco plants. A cleavable protease site was introduced at the C-terminus of γ-zein domains to recover pure calcitonin afterwards. This approach provides a high accumulation of fusion proteins within the ER and the formation of ER-derived PBs in tobacco plants. Fusion proteins were highly accumulated in ER-derived PBs in tobacco leaves. The expression level of said fusion proteins reached, in some cases, up to 12.44% of total soluble proteins. After only two purification steps, the fusion proteins were submitted to enterokinase cleavage permitting the release of calcitonin. Pure calcitonin was obtained from digestion mixture by a reverse phase chromatography. Calcitonin product accumulated in tobacco plants and was validated by mass spectroscopy. Fusion protein purification, protease digestion and full characterization of the released plant calcitonin (pCT) are also presented.

I. Experimental Procedure

Construction of Chimeric Genes and Vectors

Figure 4:
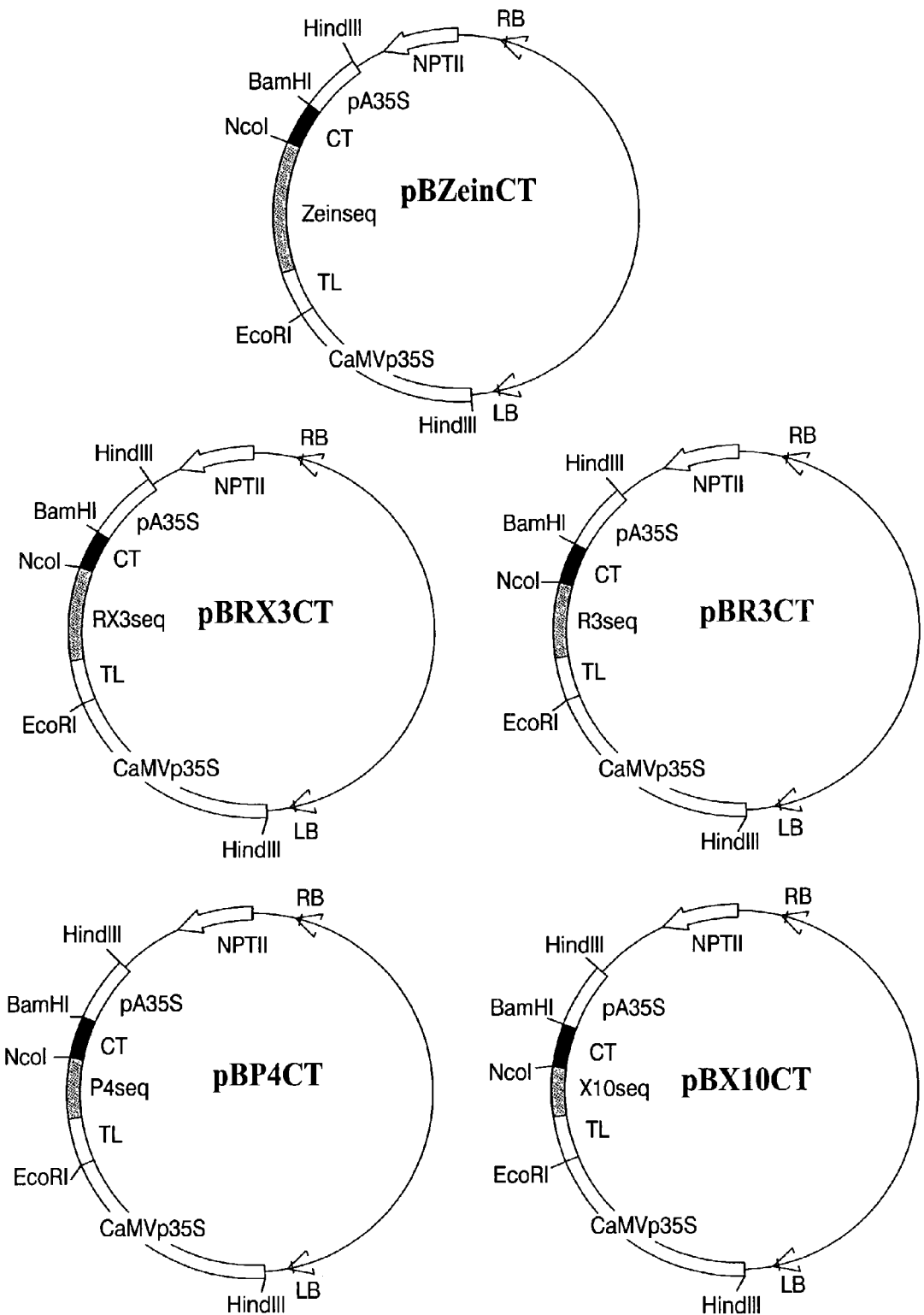
FIG. 4 shows a schematic representation of plasmids pBZeinCT, pBRX3CT, pBR3CT, pBP4CT and pBX10CT. The different plasmids are not depicted in proportion.
Figure 5:
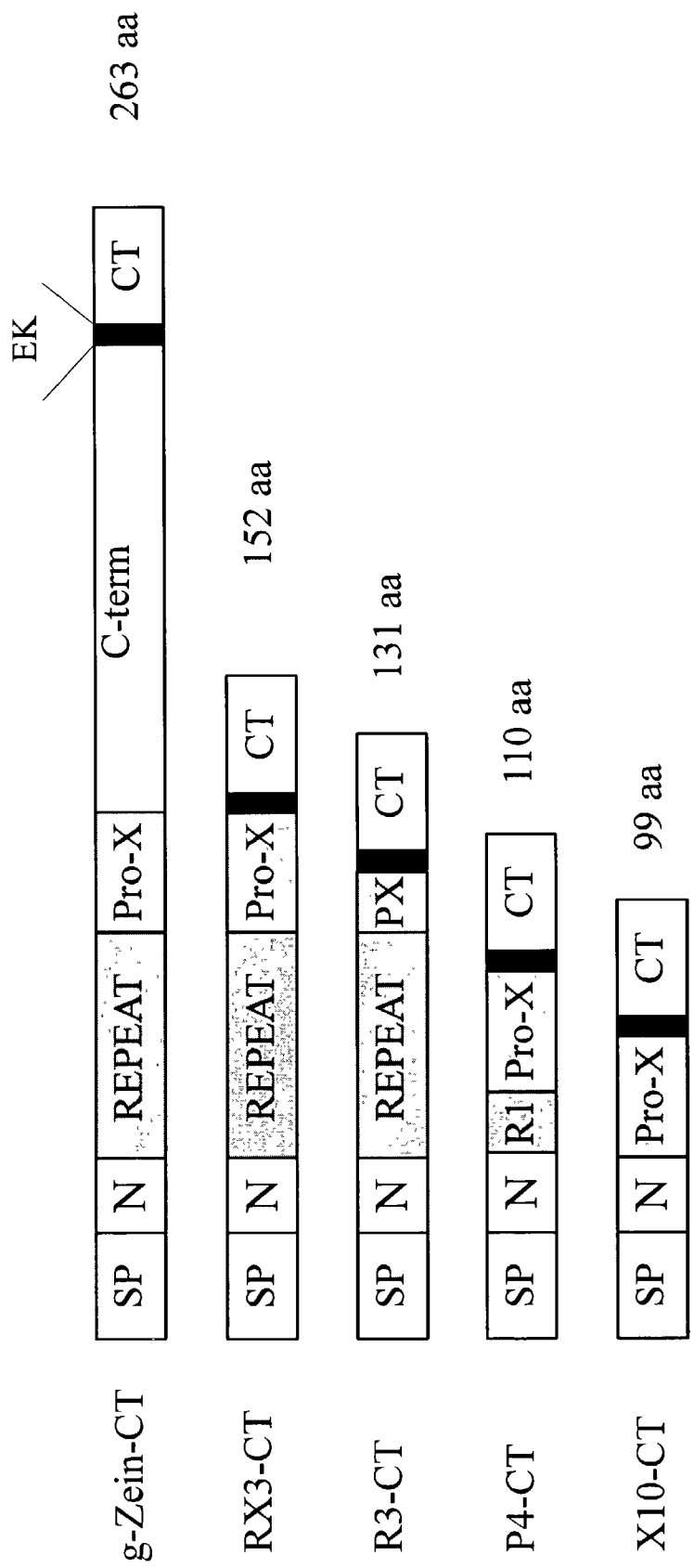
FIG. 5 shows a schematic representation of the different fusions proteins. γ-Zein and γ-zein derived domains (RX3, R3, P4 and X10) were fused to calcitonin (CT) through the enterokinase cleavable site (EK). SP, signal peptide; REPEAT, repeat domain (PPPVHL; SEQ ID NO: 17) eight units; R1, one repeat unit; Pro-X, proline-Xaa; PX, fragment of Pro-X domain; C-term, cysteine rich C-terminal domain; N, N-terminal sequence of the mature protein. Amino acids number for each fusion protein is indicated at right.
Figure 7:
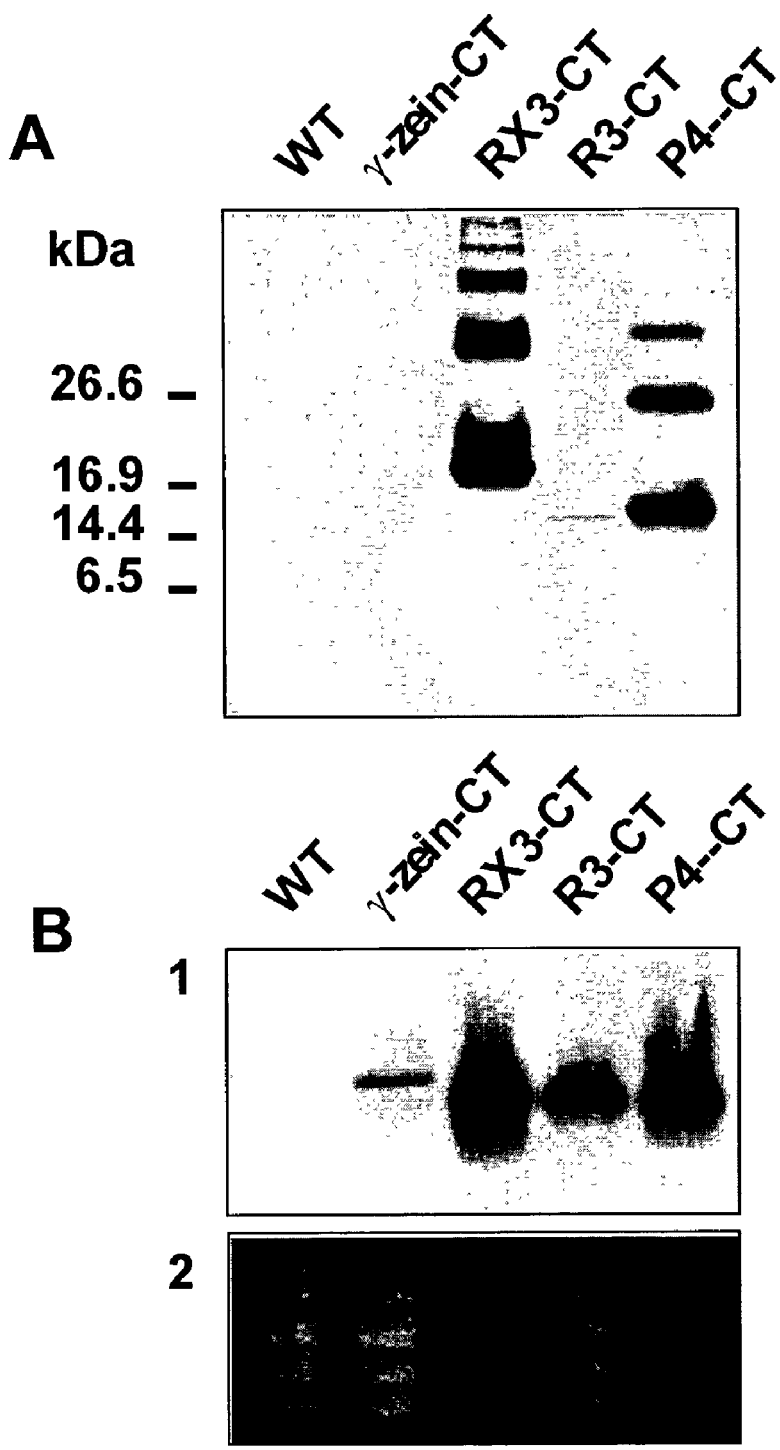
FIGS. 7A and 7B show comparative western blot analysis of the different recombinant fusion proteins using CT antiserum. Soluble protein extracts were prepared from wild type plants (WT) and transgenic tobacco lines (T1) having the maximum fusion protein expression of the related chimeric gene. 8 mg of soluble proteins were loaded on 15% SDS-polyacrylamide gel and transferred to nitrocellulose.

The wild type γ-zein gene and four γ-zein derived sequences named RX3, R3, P4 and X10 encoding different γ-zein domains (FIGS. 1A, 1B and 1C) were fused with a synthetic CT gene containing an enterokinase digestion site (FIG. 2) and introduced in plant transformation vectors as described below and in FIG. 3.

γ-Zein, RX3 and R3 cDNA sequences were generated by PCR using pKSG2 (Torrent et al., Planta 192:512-518, 1994) as template. X10 cDNA was amplified from pDR20, a plasmid produced from pKSG2 after deletion of the sequence corresponding to the repeat domain. The primers used for the different PCRs were:

for γ-zein cDNA sequence:

T1: 5'TCATGAGGGTGTTGCTCGTTGCCCTC3', (SEQ ID NO: 11)
and

T4: 5'CCATGGCGTGGGGGACACCGCCGGC3', (SEQ ID NO: 12)

for RX3 and X10 cDNA sequences:

T1 and T2:
5'CCATGGTCTGGCACGGGCTTGGATGCGG 3', (SEQ ID NO:13)
and for R3 cDNA sequence:

T1 and T3:
5'CCATGGTCCGGGGCGGTTGAGTAGGGTA3'. (SEQ ID NO:14)

The PCR products were subcloned into a pUC 18 vector (SureClone Ligation Kit, Pharmacia) and the resulting plasmids were named pUCZein, pUCRX3, pUCR3 and pUCX10. The vector pUCP4 which contains the γ-zein derived sequence P4 (FIG. 1C) was obtained during the screening of pUCRX3 derived clones. γ-zein, RX3, R3, P4 and X10 cDNA fragments, containing cohesive ends of BspHI and NcoI, were inserted into the vector pCKGFPS65C (Reichel et al., Proc. Natl. Acad. Sci. USA 93:5888-5893, 1996) previously digested with NcoI. This vector was selected because it contains the regulatory sequences for expression in plants and the GFP coding sequence that would be used for parallel targeting studies of γ-zein derived proteins in transgenic plants. The vectors generated, pCZeinGFP, pCRX3GFP, pCR3GFP, pCP4GFP and pCX10GFP contained the following regulatory sequences for expression in plant systems: i) the enhanced 35S promoter derived from the cauliflower mosaic virus (CaMVp35S), ii) the translational enhancer from tomato etch virus (TL) and iii) the transcription-termination sequence from CaMV35S (pA35S). The γ-zein derived/CT chimeric constructs were generated by substitution of the GFP coding sequence with the CT synthetic gene as described below (see FIG. 3).

The synthetic gene encoding the 32 amino acids of active salmon CT (FIG. 2) were generated from two 122 bases complementary oligonucleotides. The oligonucleotides were designed to use preferential plant codons in order to achieved high expression in plants. The 5' phosphorilated oligonucleotides synthesized using an Applied Biosystems 394 DNA synthesizer had the following sequences:

CaII:

4 CaII:
5'CATGGACGACGACGACAAGTGCTCCAACCTCTCTACCTGCGTTCTTGGTAAGCTCTCT (SEQ ID NO: 15)
CAGGAGCTTCACAAGCTCCAGACTTACCCTAGAACCAACACTGGTTCCGGTACCCCTGGT
TGAT3',

CaIII:

5 CaIII:
5'CTAGATCAACCAGGGGTACCGGAACCAGTGTTGGTTCTAGGGTAAGTCTGGAGCTTGT (SEQ ID NO: 16)
GAAGCTCCTGAGAGAGCTTACCAAGAACGCAGGTAGAGAGGTTGGAGCACTTGTCGT
CGTCGTC3'.

After purification on 12% polyacrylamide gel, 60 pmole of each oligonucleotide were used to form the double-strand molecule. Hybridation mixture heated to 95° C. for 5 min was maintained at 70° C. for 1 hour and let get cold at room temperature. The synthetic cDNA fragment contained NcoI and XbaI cohesive ends at 5' and 3' terminal respectively. The synthetic CT cDNA included a 5' linker sequence corresponding to the enterokinase specific cleavage site ((Asp)4-Lys) and was extended at 3' end to produce a single glycine for further amidation of the CT peptide. The NcoI/XbaI CT cDNA was subcloned into a pUC 18 vector and was then inserted into the NcoI and BamHI restriction sites of the vectors pCZeinGFP, pCRX3GFP, pCR3GFP, pCP4GFP and pCX10GFP containing the derived γ-zein coding sequences and deleted from the GFP coding sequence. The resulting constructs were named pCZeinCT, pCRX3CT, pCR3CT, pCP4CT and pCX10CT (FIG. 3). Effective plant transformation vectors pBZeinCT, pBRX3CT, pBR3CT, pBP4CT and pBX10CT (FIG. 4) were ultimately obtained by inserting the different HindIII/HindIII expression cassettes into the binary vector pBin19 (Bevan, Nucleic Acids Research 12:8711-8721, 1984).

Stable Tobacco Plants Transformation

Binary vectors were transferred into LBA 4404 strains of Agrobacterium tumefaciens. Tobacco (Nicotiana tobaccum, W38) leaf discs were transformed according to the method of Draper et al., in *Plant Genetic Transformation and Gene Expression, A Laboratory Manual* (Eds. J. Draper et al.), Blackwell Scientific Publications (1988). Regenerated plants were selected on medium containing 200 mg/L kanamycin and transferred to a greenhouse. Transgenic tobacco plants having the highest transgene product levels were cultivated for obtention of Ti generation. Developing leaves (approximately 12 cm long) were harvested, immediately frozen with liquid nitrogen and stored at −80° C. for further experiments.

Extraction and Western Blot Analysis of Recombinant Proteins

Tobacco leaves were ground in liquid nitrogen and homogenized using 4 ml of extraction buffer (50 mM Tris—HCl pH 8, 200 mM dithiothreitol (DTT) and protease inhibitors (10 mM aprotinin, 1 mM pepstatin, 100 mM leupeptine, 100 mM phenylmethylsulphonyl fluoride and 100 mM E64 [(N-(N-(L-3-trans-carboxyoxirane-2-carbonyl)-Lleucyl)-agmantine] per gram of fresh leaf material. The homogenates were stirred for 30 min at 4° C. and then centrifuged twice (15000 rpm 30 min, 4° C.) to remove insoluble material. Total soluble proteins were quantified using the Bradford protein assay (Bio-Rad). Proteins were separated on 15% SDS polyacrylamide gel and transferred to nitrocellulose membranes (0.22 mM) using a semidry apparatus. Membranes were incubated with γ-zein antiserum (dilution 1/7000) (Ludevid et al., Plant Sci. 41:41-48, 1985) or an antiserum raised against KLH-calcitonin (CT-antiserum) (dilution 1/1000) and were then incubated with horseradish peroxidase conjugated antibodies (dilution 1/10000). Immunoreactive bands were detected by enhanced chemiluminescence (ECL western blotting system, Amersham). Calcitonin antibodies were raised in rabbits by inoculating synthetic salmon calcitonin coupled to KLH. After four inoculations of the antigen (200 Ag each), the sera was collected, aliquoted and stored at −80° C. Sera titration were carried out by immuno-dot blots using synthetic calcitonin and ELISA assays using BSA-calcitonin as antigen.

Northern Blot Analysis

Total RNA was isolated from wild type and transgenic tobacco (T1) leaves according to Logemann et al., 1987. RNA was fractionated on denaturing formamide-agarose gel electrophoresis (30 mg per lane) and was capillary blotted onto nylon membrane (Hybond N, Amersham Pharmacia Biotech). RNA blots were hybridized with a 129-base DNA probe obtained from CT cDNA and labeled with (a-32P) dCTP using a random primed DNA labeling kit (Roche). Hybridization was carried out overnight at 42° C. and filters were washed three times for 15 min in 3× SSC and 0.5% SDS (W/V) at 65° C. Blots were detected with a phosphorimager scanner (Fluor-STM MultiImager, BIO-RAD).

ELISA Assays

ELISA assays were conducted for plant calcitonin (pCT) quantification on soluble leaf protein extracts and partially purified γ-zein-CT fusion proteins. Microtiter plates (MaxiSorp, Nalgene Nunc International) were loaded with soluble proteins (100 ml) diluted in phosphate-buffered saline pH 7.5 (PBS) and incubated overnight at 4° C. After washing the wells three times, unspecific binding sites were blocked with 3% bovine serum albumin (BSA) in PBS-T (PBS containing 0.1% Tween 20), one hour at room temperature. The plates were incubated with CT antiserum (dilution 1/1000) for two hours and after four washes with PBS-T, incubated with peroxidase-conjugated secondary antibodies (dilution 1/8000) (Sigma) for two hours. Primary and secondary antibodies were diluted in PBS-T containing 1% BSA. After washing extensively with PBS-T, the enzymatic reaction was carried out at 37° C. with 100 ml of substrate buffer (100 mM sodium acetate pH 6, 0.01 mg/ml TMB (3,3',5,5'-tetramethylbenzidine) and 0.01% hydrogen peroxide). The reaction was stopped after 10 min with 2N sulfuric acid and the optical density was measured at 450 nm using a Multiskan EX spectrophotometer (Labsystems). The antigen concentration in plant extracts was extrapolated from a standard curve obtained by using calcitonin-BSA and CT antiserum (dilution 1/1000).

Electron Microscopy

Leaves from wild-type and transgenic plants were fixed by vacuum infiltration with 1% glutaraldehyde and 2.5% paraformaldehyde in 20 mM phosphate buffer, pH 7.4 for one hour at room temperature. After washing with 20 mM phosphate buffer and 200 mM ammonium chloride successively, samples were dehydrated through ethanol series and embedded in Lowicryl K4M resin. Immunochemistry was performed essentially as described by Moore et al., 1991. Ultrathin sections were incubated with antisera against, KLH-calcitonin (1/500), aBiP (1/500) and γ-zein (1/1500). Protein A-colloidal gold (gold particles of 15 nm) was used for antibody detection. As a control, parallel incubations were carried out on non-transgenic plant samples using identical dilutions of primary antibodies and on transgenic samples without primary antibody. Sections were stained with uranyl acetate and lead citrate and examined with a model 301 electron microscope (Phillips, Eindhoven, The Netherlands).

Purification and Enterokinase Cleavage of RX3-CT and P4-CT Fusion Proteins

Soluble extracts of RX3-CT and P4-CT were obtained from leaves of transgenic tobacco plants (T1) in extraction buffer as described above. Solid (NH4)2SO4 was progressively added at 0° C. to RX3-CT and P4-CT soluble extracts to 45% and 60% saturation respectively. The samples were stirred for 30 min at 0° C. and were then centrifuged at 15000 rpm for 45 min at 4° C. The precipitated proteins were resuspended in 20 mM Tris—HCl pH 8.6 and desalted on PD 10 column (Sephadex G-25 M, Amersham Pharmacia). Desalted protein extracts were fractionated by Fast Performance Liquid Chromatography (FPLC) using an anion exchange column (HiTrap Q sepharose, Amersham Pharmacia) equilibrated with 20 mM Tris—HCl pH 8.6, 100 mM DTT. Protein elution was carried out with a linear salt gradient from 0 to 200 mM NaCl in 20 mM Tris—HCl pH 8.6, 100 mM DTT. The presence of RX3-CT and P4-CT in eluted fractions was assessed by 15% SDS polyacrylamide gel electrophoresis and immunoblot detection using CT antiserum. Positive fractions were desalted and concentrated with 5 K NMWL centrifugal filters (BIOMAX, Millipore). Quantification of RX3-CT and P4-CT fusion proteins was performed by ELISA.

For EK digestion, 15 mg of partially purified fusion proteins were incubated with 0.2 U EK (EK Max, Invitrogen) in 30 ml of digestion buffer (50 mM Tris—HCl pH8, 1 mM NaCl, 0.1% Tween-20) for 24 hours at 20° C. EK digestion buffer was supplemented with 100 mM DTT. The presence of the reducing agent allows to optimize enterokinase cleavage. Digestion products were analyzed on 18% Tris-Tricine polyacrylamide gel electrophoresis and released pCT was detected by immunoblot. Synthetic salmon CT was used as positive control.

Purification and Analysis of Released pCT

Plant calcitonin (pCT) released from fusion proteins by EK digestion was purified by RP-HPLC. Digestion mixture was applied to an analytical RP-C18 column (250×4 mm, 10 mM particule size, 120 Å pore size) and the column was eluted using a gradient ranging from 25 to 60% acetonitrile with 0.036% TFA in 20 min at a flow rate of 1 ml/min. The fractions collected were concentrated by lyophilization and stored at −20° C. for pCT characterization. In a separate experiment, standard salmon CT was eluted under the same chromatographical conditions. TOF-MALDI mass spectrometry was used for pCT characterization. RP-HPLC fraction aliquots were mixed with equal volume of a matrix solution (10 mg/ml a-cyano-4-hydroxycinnamic acid and 0.1% TFA) and 1 ml of the mixture was deposited on the holder and analyzed with a Voyager-DE-RP mass spectrometer (Applied Biosystems). Standard salmon CT was always used in TOF-MALDI mass spectrometry experiments as a control. C-terminal analysis of the pCT was performed by incubating the purified peptide (20 pmoles/ml) for 60 min at 37° C. with carboxypeptidase Y (0.1U/ml) and analysis of the digestion products by TOF-MALDI mass spectrometry.

II. Results

Construction of several derived γ-zein-CT chimeric genes

Figure 8:
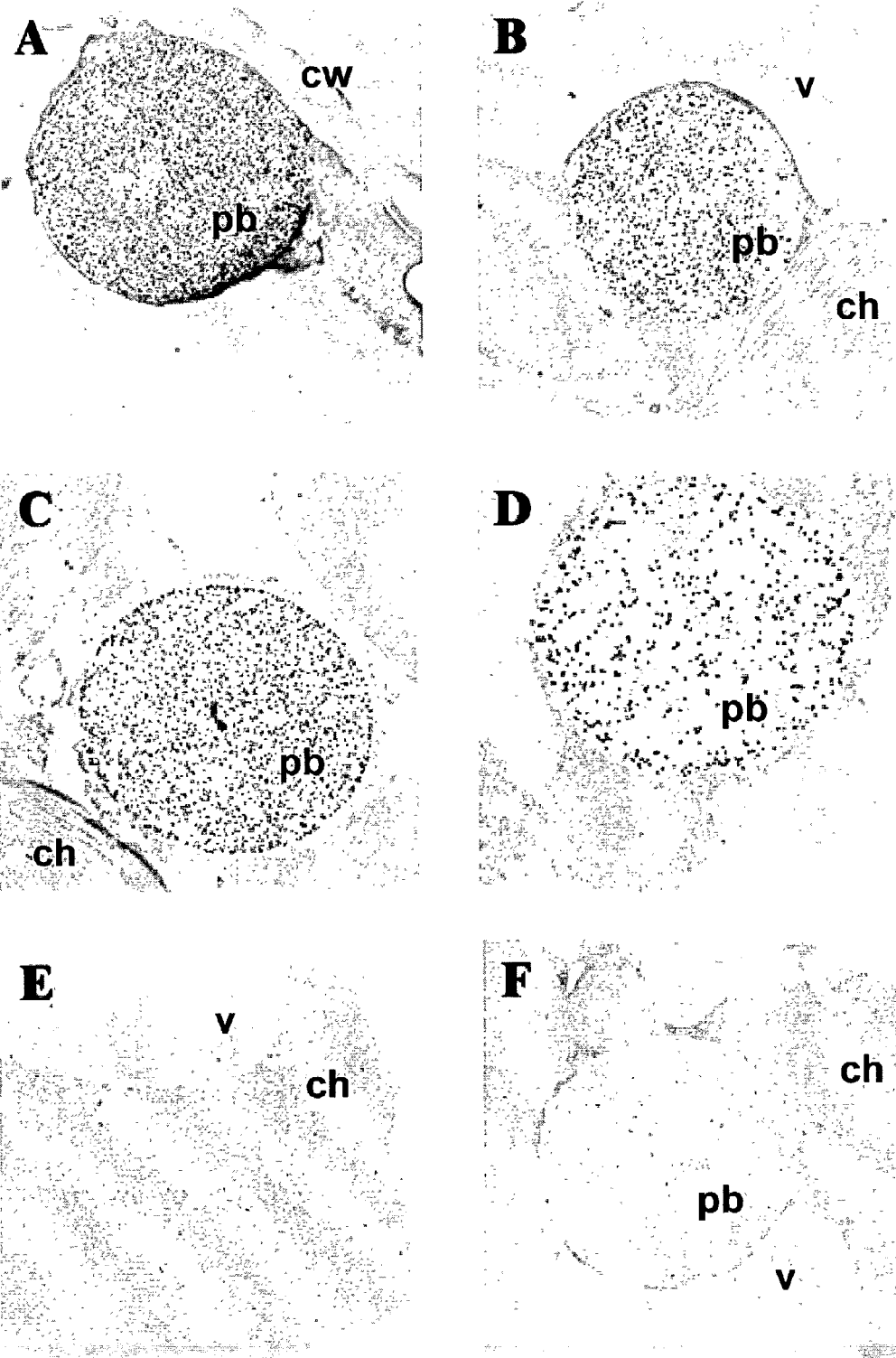
FIGS. 8A, 8B, 8C, 8D, 8E and 8F show the subcellular localization of RX3-CT and P4-CT proteins in transgenic tobacco plants. Specifically.

The expression and successful assembly of γ-zein proline rich domains into ER-derived protein bodies in plant leaves (Geli et al., 1994) provide a valuable tool to accumulate therapeutic proteins in the ER of plant tissues. γ-Zein gene was deleted to create various proline-rich truncated proteins used as fusion partner to produce CT in tobacco plants. The chimeric genes comprised the γ-zein domains and a CT synthetic gene linked by a linker corresponding to a protease cleavable site. The synthetic gene encoding the 32 amino acids active salmon calcitonin was generated from two complementary oligonucleotides (122 bases) designed to use preferential plant codons in order to achieve high expression of the recombinant peptide in plants. The synthetic CT cDNA (FIG. 2) included at 5' end a linker sequence corresponding to the enterokinase cleavage site ((Asp)4-Lys) and at 3' end an additional codon to produce a glycine. This glycine is a necessary substrate for the amidating enzyme (PAM) to generate the C-terminal prolinamide essential for CT biological activity. The calcitonin cDNA was fused to the sequences encoding the γ-zein domains in a C-terminal fusion. For optimal expression of the derived γ-zein-CT chimeric genes in plant systems, the plant transformation vectors contained the following regulatory sequences i) the constitutive enhanced 35S promoter and the 35S terminator from the cauliflower mosaic virus and ii) the translational enhancer from tomato etch virus (TL). The different fusion proteins generated are represented in FIG. 5. The γ-zein-CT fusion protein contains the whole γ-zein fused to CT. The RX3-CT, R3-CT, P4-CT and X10-CT fusion proteins contain the derived γ-zein domains linked to CT in the same way as whole γ-zein. These fusion proteins differ essentially in the presence or the absence of the repeat and prox domains.

Production of Fusion Proteins in Tobacco Plants

All the fusion genes were used for stably tobacco plant transformation via Agrobacterium tumefaciens. At least twenty independent kanamycin-resistant plants (To) were regenerated for each fusion gene. The screening of the transgenic plants was performed by western blot analysis of soluble proteins extracts using a γ-zein polyclonal antiserum. Transgenic lines immunoblot pattern representatives of each fusion gene are shown in the FIG. 6. As observed, recombinant fusion proteins were obtained in all transgenic lines with the exception of the X10-CT fusion gene where no traces of fusion proteins were detected. This small fusion protein (80 amino acids) is probably unstable in tobacco plants. Two immuno-labelled bands were detected in the R3-CT transgenic lines, one with an atypical high apparent molecular mass. This fusion protein was probably subjected to post-traductional modifications such as glycosylation. Indeed, it has been demonstrated that the γ-zein proline rich repeat domain is able to be glycosilated when expressed in Arabidopsis plants (Alvarez et al., Planta 205:420-427, 1998). Protein expression level was quite variable between the different lines of a same fusion gene with the exception of the RX3-CT fusion gene which showed a high recombinant protein expression level in all transgenic lines. An additional immunoblot screening was carried out using an antiserum specifically raised against the sCT peptide (FIG. 7A). As observed, the RX3-CT and the P4-CT proteins were strongly recognized by the sCT antiserum indicating that these fusions provide a better accumulation of the CT peptide in tobacco plants. It could be noted that RX3-CT and P4-CT immunoblot patterns displayed several labelled bands, the major band corresponding to the correct apparent molecular mass of the related recombinant protein. One hypothesis could be that the high molecular weight labelled bands were the result of an oligomerization process on γ-zein domains which formed during the accumulation of the fusion proteins in plants tissues. In order to check the expression levels of fusion genes in relation to protein levels, a comparative northern blot analysis (FIG. 7B) was performed using the transgenic lines analyzed by immunoblot in FIG. 7A. As shown, RX3-CT and P4-CT transcripts were the more abundant demonstrating a stable accumulation of these transcripts. Surprisingly, R3-CT transcripts were relatively abundant in comparison to the low R3-CT fusion protein level detected by immunoblot. Probably, the post-translational modification avoids the correct self-assembly of the fusion protein and subsequently its stability in the ER.

The maximum expression level of RX3-CT and P4-CT proteins, measured by ELISA on leaf protein extracts from T1 plants, were respectively 12.44% and 10.65% of total soluble proteins whereas γ-zein-CT and R3-CT expression level remained as lower as 0.01% of total soluble proteins. With regard to these results, RX3-CT and P4-CT transgenic lines were chosen for further experiments conducing to the production of plant calcitonin (pCT).

Subcellular Localization of Fusion Proteins RX3-CT and P4-CT

Expression of γ-zein and two γ-zein deletion mutans in Arabidopsis plants demonstrated that these proteins located within the ER of mesophyl cells forming ER-derived PBs (Geli et al., Plant Cell 6:1911-1922, 1994). It was not evident, however, that the calcitonin fused to γ-zein derivatives was sorted to similar organelles, the ER-PBs. To examine the subcellular localization in tobacco leaves of the γ-zein fusion proteins containing calcitonin, immunoelectron microscopy (FIG. 8) was used. Ultra thin sections of transgenic tobacco leaves expressing RX3-CT and P4-CT proteins, were incubated with CT antibody and protein A-gold. A large PB-like organelles strongly labelled were observed in mesophyl cells of tobacco expressing RX3-CT and P4-CT (FIGS. 8A and 8B, respectively). Few vesicles were detected per cell and their size was quite heterogeneous. Since fusion proteins contained calcitonin protein and γ-zein fragments, the ultrathin sections were also incubated with γ-zein antibody. As was expected, the PBs were labeled with γ-zein antibody confirming that the fusion proteins accumulated inside these organelles (FIG. 8C). To demonstrate that the PBs were formed from the ER, the sections were incubated with an antibody against the ER resident protein, BiP (FIG. 8D). The concomitant occurrence of the CT-fusion proteins and BiP in these organelles indicated that RX3-CT and P4-CT accumulated within the ER lumen to form further independent ER-derived vesicles. Since PB-like organelles were not detected in ultrathin sections of non-transgenic plants (FIG. 8E), the control experiments were performed without primary antibody in transgenic plants (FIG. 8F). As expected no specific label was detected in control experiments.

Purification of Fusion Proteins and Release of pCT

Figure 9:
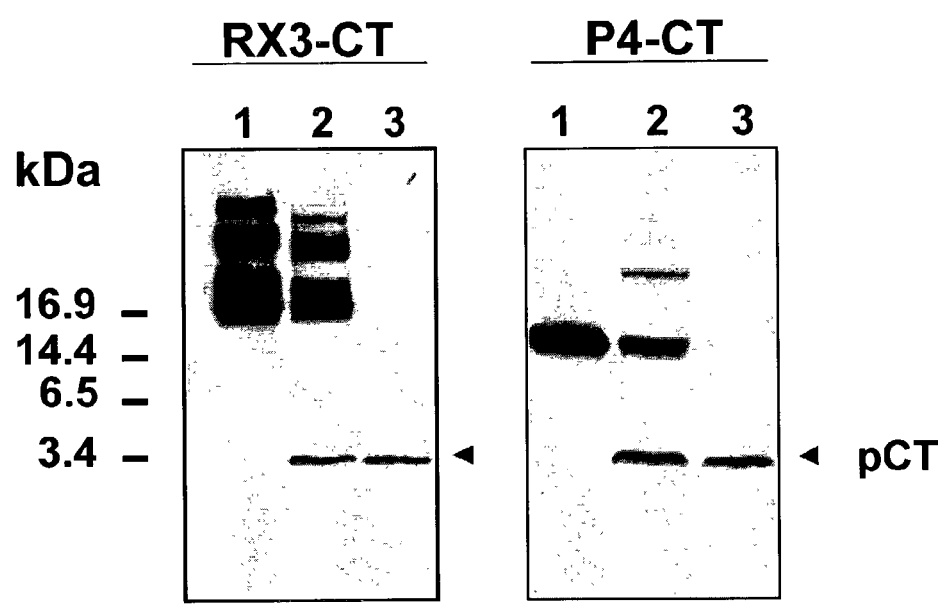
FIG. 9 shows the results of the immunoblot analysis of RX3-CT and P4-CT fusion protein EK cleavage. 12 mg of each partially purified fusion protein were incubated with 0.2 U EK during 24 hours at 20° C. Digested fusion proteins were fractionated on 18% Tris-Tricine polyacrylamide gel electrophoresis and transferred to nitrocellulose. Lanes 1, non digested fusion proteins (1 mg); lanes 2, digestion products; lanes 3, synthetic salmon CT standard.

RX3-CT and P4-CT fusion proteins were effectively extracted from transgenic tobacco leaves (T1) using an extraction buffer including a reducing agent such as DTT (200 mM). About 85 mg of RX3-CT and 73 mg of P4-CT were recovered per gram of fresh material. RX3-CT and P4-CT proteins were concentrated respectively by 45% and 60% ammonium sulfate precipitation. The desalted protein extracts were fractionated by FPLC using an anion exchange chromatography and the recovered fusion proteins were quantified by ELISA. RX3-CT protein represented about 80% of total purified proteins whereas P4-CT was only about 50% of total purified proteins. Such difference could be explained by the fact that more proteins precipitate at 60% of ammonium sulfate than at 45% and that consequently the precipitated P4-CT proteins contained much more contaminant proteins. The partially purified fusion proteins RX3-CT and P4-CT were digested by EK and pCT release was controlled by a Tris-Tricine polyacrylamide gel electrophoresis and immunodetection. As shown in FIG. 9, a single labelled band corresponding to calcitonin was generated from both RX3-CT and P4-CT protein cleavage. Small amounts of fusion proteins RX3-CT and P4-CT remained undigested probably due to the non accessibility of the enzyme to some cleavage sites.

Purification and Characterization of pCT

Figure 10:
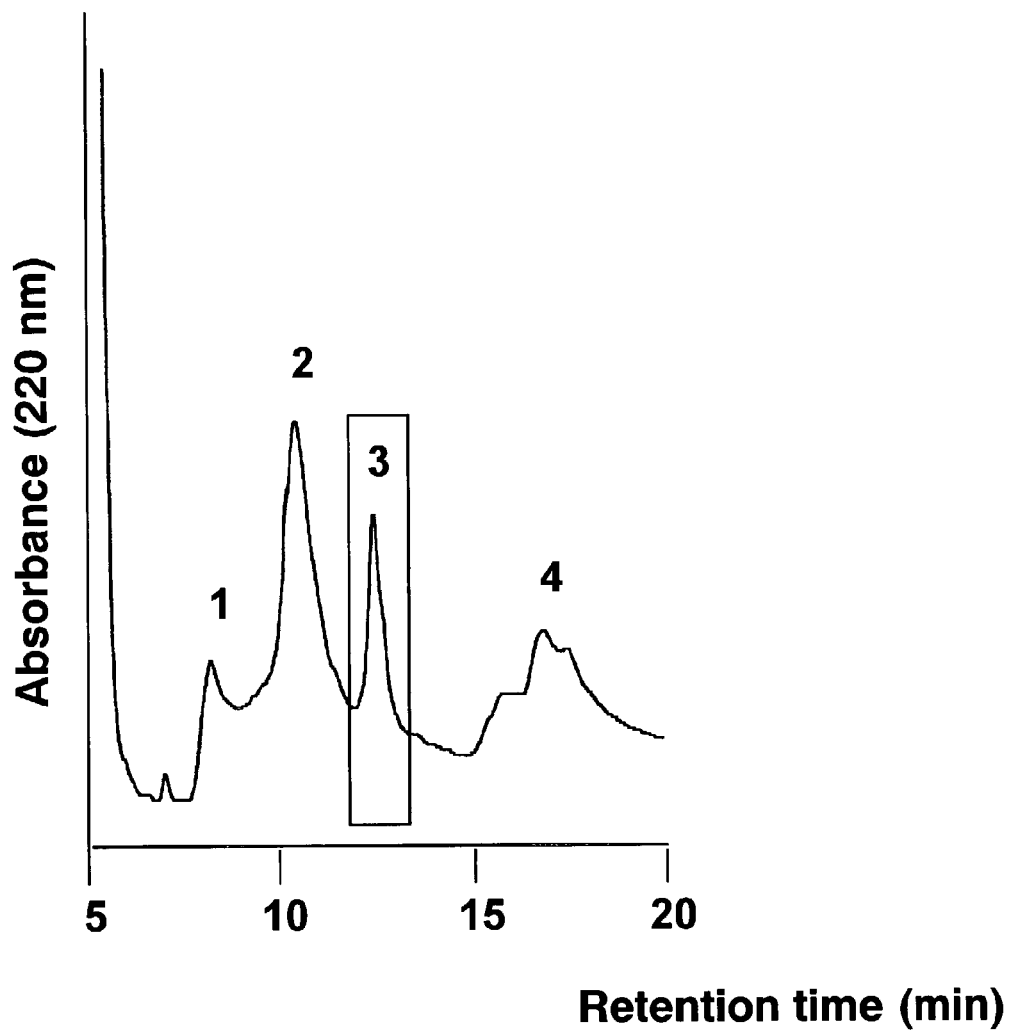
FIG. 10 shows the results of RP-HPLC fractionation of RX3-CT fusion protein digested by EK. pCT released from RX3-CT fusion protein was detected in fraction 3 (Tr=13 min) by TOF-MALDI using synthetic salmon CT as standard.
Figure 11:
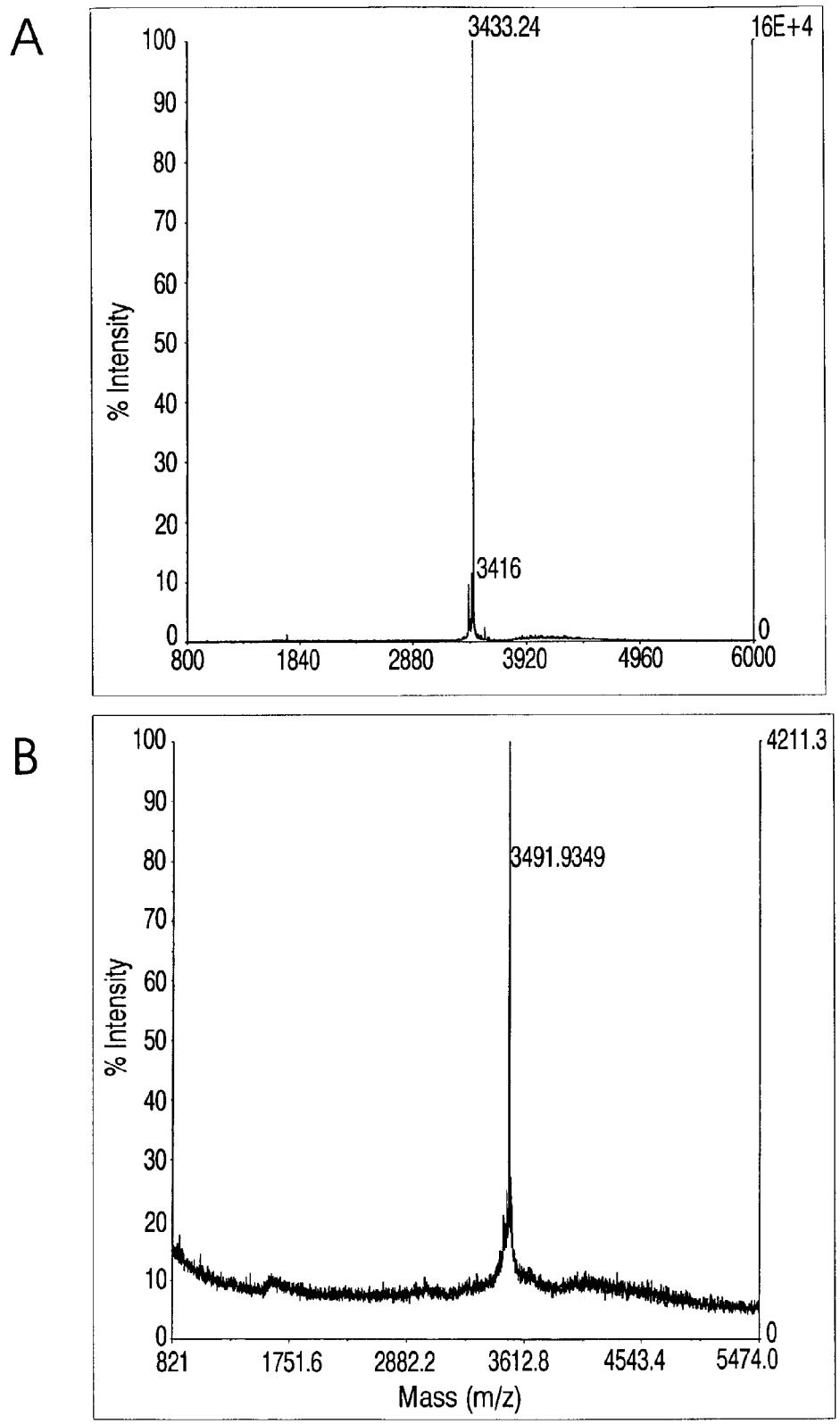
FIGS. 11A and 11B show the results of TOF-MALDI mass spectrometry characterization of (11A) synthetic salmon CT (MW=3433.24) and (11B) plant CT (MW=3491.93) eluted at Tr=13 min from the RP-HPLC fractionation.

Plant calcitonin (pCT) was isolated by fractionation of the EK digestion mixtures on an analytical C18 RP-HPLC column (FIG. 10) and analysis of the eluted fractions by TOF-MALDI mass spectrometry using synthetic sCT as standard (MW 3433.24, FIG. 11A). pCT calcitonin was eluted at 13 min (synthetic sCT Tr=14 min) and gave a single spectrum with a mass of 3491.93 Da by TOF-MALDI mass spectrometry that is consistent with the theoretical molecular mass of the reduced C-terminal glycine-extented calcitonin (FIG. 11B). Mass spectrometry analysis of pCT subjected to carboxypeptidase Y digestion confirmed the integrity of the C-terminal glycine that is essential to produce the C-terminal prolinamide.

III. Discussion

A successful fusion protein-based system to accumulate salmon calcitonin in tobacco plants is presented. Two fusion proteins RX3-Cal and P4-Cal were found to strongly accumulate in ER-derived PBs of tobacco leaves. These fusion proteins contain the CT peptide and the proline rich domains of γ-zein which consist in i) the repeat domain composed of eight units of the hexapeptide PPPVHL (SEQ ID NO: 17; only one unit in P4-Cal fusion protein) and ii) the proX domain where proline residues alternate with other amino acids. The γ-zein proline rich domains are necessary for the correct retention and assembly of γ-zein within Arabidopsis plants ER (Geli et al., Plant Cell 6:1911-1922, 1994). The folding and the stabilization of the γ-zein polypeptide chains in the ER have been attributed to the ability of the repeat and prox domains to self-assemble and to promote the formation of oligomers. The particular conformation adopted by these highly hydrophobic domains would be due to the proline rich sequences which are able to form an amphipathic secondary structure. As a result of its proper conformation, the proline rich domains would induce aggregation mechanisms involving protein-protein interactions and disulphide cross-links conducing to the ER retention and the formation of ER-derived PBs. This example shows that when expressed in a N-terminal fusion manner the γ-zein proline rich domains conserve the whole capacity to self-assemble and to promote the complex events which lead to the retention and the accumulation in the ER-derived PBs. The salmon CT involved in the fusion protein was also found to greatly accumulate in the PBs. The high expression level of CT in the transgenic tobacco plants can be attributed to the ability of the proline rich domains to fold and to stabilize the fusion protein. The deposition of the fusion protein in the PBs certainly contribute to the enrichment of the plant tissues in CT by removing it from the hydrolytic intracellular environment. As small peptides are unstable in biological systems the fusion protein approach has been currently used to produce calcitonin in heterologous systems, for example in *E. coli* (Ray et al., Bio/Technology 11:64-70, 1993; Yabuta et al., Appl. Microbiol. Biotechnol. 42 (5):703-708, 1995; Hong et al., Biochem. Biophys. Res. Com. 267:362-367, 2000), in Staphylococcus carnosus (Dilsen et al., Appl. Microbiol. Biotechnol. 54:361-369, 2000) and in the milk of transgenic rabbits (Mckee et al., Nature Biotechnology 16:647-651, 1998). In this last case, the fusion of CT with human alpha lactalbumin had also the purpose to mask the calcitonin activity to avoid a possible interference with the normal animal development.

In summary, the practice of the present invention succeeded in rapid production of glycine extended sCT from tobacco plants:

i) RX3-Cal and P4-Cal fusion proteins were efficiently recovered from tobacco tissues because of their high solubility in the presence of reducing agents;

ii) enterokinase release of calcitonin from the fusion proteins was accomplished after one purification step of the fusion protein by an anion exchange chromatography; and iii) a reverse phase chromatography led to purified CT by removing it from EK digestion mixture.

Mass spectrometry analysis of the released CT confirmed that correct glycine extended CT was produced by the tobacco plants.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A nucleic acid molecule comprising (a) a first nucleic acid sequence comprising a nucleotide sequence that encodes a fragment of a gamma-zein protein that directs a protein to and retains said protein towards the endoplasmic reticulum (ER) of a plant cell and accumulates said protein as ER-derived protein bodies, said first nucleic acid sequence consisting of a sequence that encodes a repeat domain of SEQ ID NO:17 of the gamma-zein protein and a nucleotide sequence that encodes the N-terminal nine residues to all of the ProX domain of the gamma-zein protein; and (b) a second nucleic acid sequence that encodes calcitonin as a peptide or protein of interest, wherein the 3' end of said first nucleic acid sequence is linked to the 5' end of said second nucleic acid sequence.

2. The nucleic acid molecule of claim 1, wherein said first nucleic acid sequence is SEQ ID NO: 3 or SEQ ID NO: 7.

3. The nucleic acid molecule of claim 1, wherein second nucleic acid sequence comprises a nucleotide sequence encoding calcitonin and a codon for glycine at the 3' end of said nucleic acid sequence encoding calcitonin.

4. A nucleic acid construct comprising: (i) the nucleic acid molecule of claim 1, and (ii) a regulatory nucleotide sequence that regulates the transcription of the nucleic acid molecule of (i), wherein said regulatory nucleotide sequence is functional in plants.

5. The nucleic acid construct of claim 4, wherein said regulatory nucleotide sequence is tissue-specific.

6. The nucleic acid construct of claim 4, wherein said regulatory nucleotide sequence comprises a promoter functional in plants.

7. The nucleic acid construct of claim 4, wherein said regulatory nucleotide sequence comprises a nucleotide sequence selected from the group consisting of a 35SCaMV promoter, a patatina promoter, a storage protein promoter, a ubiquitine gene promoter, and a gamma-zein gene regulatory sequence.

8. The nucleic acid construct of claim 4, wherein said regulatory nucleotide sequence comprises a transcription termination sequence functional in plants.

9. The nucleic acid construct of claim 8, wherein said regulatory nucleotide sequence comprises a transcription termination sequence selected from the group consisting of a 35SCaMV terminator, an octopine synthase (ocs) gene terminator, a nopaline synthase (nos) gene terminator, and a gamma-zein gene terminator.

10. The nucleic acid construct of claim 4, wherein said regulatory nucleotide sequence comprises a translation enhancer functional in plants.

11. The nucleic acid construct of claim 10, wherein said translation enhancer functional in plants comprises the tomato etch virus translation enhancer.

12. A vector comprising the nucleic acid molecule of claim 1 or the nucleic acid construct of claim 4.

13. A method for producing a peptide or a protein of interest in a plant host system that comprises growing a plant host system that has been transformed with the nucleic acid molecule of claim 1 under conditions that allow the production and expression of said peptide or protein of interest in the form of a fusion protein.

14. A method for producing a peptide or a protein of interest in a plant host system that comprises growing a plant host system that has been transformed with the nucleic acid molecule of claim 1 in which the nucleic acid is integrated into the genome under conditions that allow the production and expression of said protein or peptide of interest in the form of a fusion protein.

15. The method of claim 13 that further comprises the isolation and purification of said fusion protein.

16. A method for producing a calcitonin-containing fusion protein in a plant host system comprising the steps of:
 a) transforming a plant host system with an expression vector or with a nucleic acid construct comprising a regulatory sequence for the transcription of a nucleic acid molecule operatively linked to a nucleic acid molecule of claim 1;
 b) generating complete plants from said plant host systems transformed with said expression vector or nucleic acid construct;
 c) growing such transformed plants under conditions that allow the production and expression of calcitonin in the form of a fusion protein; and optionally
 d) isolating, and purifying said fusion protein and treating said fusion protein in order to release calcitonin.

17. The method of claim 16, wherein said first nucleic acid sequence encodes full length gamma-zein protein.

18. The method of claim 16, wherein said first nucleic acid sequence encodes a fragment of gamma-zein protein.

19. The nucleic acid molecule of claim 1 that further comprises a third nucleotide sequence that encodes an amino acid sequence that is specifically cleavable by enzymatic means, said third nucleic acid sequence being located between said first and second named nucleic acid sequences.

20. The nucleic acid molecule of claim 19, wherein said third nucleic acid sequence encodes an amino acid sequence that defines a protease cleavage site.

21. The nucleic acid molecule of claim 20, wherein said protease cleavage site is an enterokinase cleavage site.

* * * * *

SEQUENCE LISTING

<160> NUMBER OF SEQ ID NOS: 16

<210> SEQ ID NO 1
<211> LENGTH: 672
<212> TYPE: DNA
<213> ORGANISM: Zea mays
<220> FEATURE:
<221> NAME/KEY: CDS
<222> LOCATION: (1)..(672)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | agg | gtg | ttg | ctc | gtt | gcc | ctc | gct | ctc | ctg | gct | ctc | gct | gcg | agc | 48 |
| Met | Arg | Val | Leu | Leu | Val | Ala | Leu | Ala | Leu | Leu | Ala | Leu | Ala | Ala | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | acc | tcc | acg | cat | aca | agc | ggc | ggc | tgc | ggc | tgc | cag | cca | ccg | ccg | 96 |
| Ala | Thr | Ser | Thr | His | Thr | Ser | Gly | Gly | Cys | Gly | Cys | Gln | Pro | Pro | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| ccg | gtt | cat | cta | ccg | ccg | gtg | cat | ctg | cca | cct | ccg | gtt | cac | ctg | | 144 |
| Pro | Val | His | Leu | Pro | Pro | Val | His | Leu | Pro | Pro | Pro | Val | His | Leu | | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | cct | ccg | gtg | cat | ctc | cca | ccg | gtc | cac | ctg | ccg | ccg | gtc | | | 192 |
| Pro | Pro | Pro | Val | His | Leu | Pro | Pro | Val | His | Leu | Pro | Pro | Val | | | |
| 50 | | | | | 55 | | | | | 60 | | | | | | |

| | | | | | | | | | | | | | | | | |
|---|---|---|---|---|---|---|---|---|---|---|---|---|---|---|---|---|
| cac | ctg | cca | ccg | ccg | gtc | cat | gtg | ccg | ccg | ccg | gtt | cat | ctg | ccg | ccg | 240 |
| His | Leu | Pro | Pro | Pro | Val | His | Val | Pro | Pro | Pro | Val | His | Leu | Pro | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cca | cca | tgc | cac | tac | cct | act | caa | ccg | ccc | cgg | cct | cag | cct | cat | ccc | 288 |
| Pro | Pro | Cys | His | Tyr | Pro | Thr | Gln | Pro | Pro | Arg | Pro | Gln | Pro | His | Pro | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | cca | cac | cca | tgc | ccg | tgc | caa | cag | ccg | cat | cca | agc | ccg | tgc | cag | 336 |
| Gln | Pro | His | Pro | Cys | Pro | Cys | Gln | Gln | Pro | His | Pro | Ser | Pro | Cys | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | cag | gga | acc | tgc | ggc | gtt | ggc | agc | acc | ccg | atc | ctg | ggc | cag | tgc | 384 |
| Leu | Gln | Gly | Thr | Cys | Gly | Val | Gly | Ser | Thr | Pro | Ile | Leu | Gly | Gln | Cys | |
| | | | 115 | | | | | 120 | | | | | 125 | | | |

| | | | | | | | | | | | | | | | | |
|---|---|---|---|---|---|---|---|---|---|---|---|---|---|---|---|---|
| gtc | gag | ttt | ctg | agg | cat | cag | tgc | agc | ccg | acg | gcg | acg | ccc | tac | tgc | 432 |
| Val | Glu | Phe | Leu | Arg | His | Gln | Cys | Ser | Pro | Thr | Ala | Thr | Pro | Tyr | Cys | |
| 130 | | | | | 135 | | | | | 140 | | | | | | |

| | | | | | | | | | | | | | | | | |
|---|---|---|---|---|---|---|---|---|---|---|---|---|---|---|---|---|
| tcg | cct | cag | tgc | cag | tcg | ttg | cgg | cag | cag | tgt | tgc | cag | cag | ctc | agg | 480 |
| Ser | Pro | Gln | Cys | Gln | Ser | Leu | Arg | Gln | Gln | Cys | Cys | Gln | Gln | Leu | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cag | gtg | gag | ccg | cag | cac | cgg | tac | cag | gcg | atc | ttc | ggc | ttg | gtc | ctc | 528 |
| Gln | Val | Glu | Pro | Gln | His | Arg | Tyr | Gln | Ala | Ile | Phe | Gly | Leu | Val | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | tcc | atc | ctg | cag | cag | cag | ccg | caa | agc | ggc | cag | gtc | gcg | ggg | ctg | 576 |
| Gln | Ser | Ile | Leu | Gln | Gln | Gln | Pro | Gln | Ser | Gly | Gln | Val | Ala | Gly | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| ttg | gcg | gcg | cag | ata | gcg | cag | caa | ctg | acg | gcg | atg | tgc | ggc | ctg | cag | 624 |
| Leu | Ala | Ala | Gln | Ile | Ala | Gln | Gln | Leu | Thr | Ala | Met | Cys | Gly | Leu | Gln | |
| | | | 195 | | | | | 200 | | | | | 205 | | | |

| | | | | | | | | | | | | | | | | |
|---|---|---|---|---|---|---|---|---|---|---|---|---|---|---|---|---|
| cag | ccg | act | cca | tgc | ccc | tac | gct | gct | gcc | ggc | ggt | gtc | ccc | cac | gcc | 672 |
| Gln | Pro | Thr | Pro | Cys | Pro | Tyr | Ala | Ala | Ala | Gly | Gly | Val | Pro | His | Ala | |
| | | 210 | | | | | 215 | | | | | 220 | | | | |

<210> SEQ ID NO 2
<211> LENGTH: 224
<212> TYPE: PRT
<213> ORGANISM: Zea mays

<400> SEQUENCE: 2

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Pro Val His Leu
        35                  40                  45

Pro Pro Pro Val His Leu Pro Pro Val His Leu Pro Pro Pro Val
50                  55                  60

His Leu Pro Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
            115                 120                 125

Val Glu Phe Leu Arg His Gln Cys Ser Pro Thr Ala Thr Pro Tyr Cys
        130                 135                 140

Ser Pro Gln Cys Gln Ser Leu Arg Gln Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
            195                 200                 205

Gln Pro Thr Pro Cys Pro Tyr Ala Ala Ala Gly Gly Val Pro His Ala
            210                 215                 220

<210> SEQ ID NO 3
<211> LENGTH: 339
<212> TYPE: DNA
<213> ORGANISM: Zea mays
<220> FEATURE:
<221> NAME/KEY: CDS
<222> LOCATION: (1)..(339)
<223> OTHER INFORMATION:

<400> SEQUENCE: 3 atg agg gtg ttg ctc gtt gcc ctc gct ctc ctg gct ctc gct gcg agc        48
Met Arg Val Leu Leu Val Ala Leu Ala Leu Leu Ala Leu Ala Ala Ser
1               5                   10                  15 gcc acc tcc acg cat aca agc ggc ggc tgc ggc tgc cag cca ccg ccg        96
Ala Thr Ser Thr His Thr Ser Gly Gly Cys Gly Cys Gln Pro Pro Pro
            20                  25                  30 ccg gtt cat cta ccg ccg ccg gtg cat ctg cca cct ccg gtt cac ctg       144
Pro Val His Leu Pro Pro Pro Val His Leu Pro Pro Pro Val His Leu
        35                  40                  45 cca cct ccg gtg cat ctc cca ccg ccg gtc cac ctg ccg ccg ccg gtc       192
Pro Pro Pro Val His Leu Pro Pro Pro Val His Leu Pro Pro Pro Val
50                  55                  60 cac ctg cca ccg ccg gtc cat gtg ccg ccg ccg gtt cat ctg ccg ccg       240
His Leu Pro Pro Pro Val His Val Pro Pro Pro Val His Leu Pro Pro
65                  70                  75                  80 cca cca tgc cac tac cct act caa ccg ccc cgg cct cag cct cat ccc       288
Pro Pro Cys His Tyr Pro Thr Gln Pro Pro Arg Pro Gln Pro His Pro
                85                  90                  95
```

```
cag cca cac cca tgc ccg tgc caa cag ccg cat cca agc ccg tgc cag      336
Gln Pro His Pro Cys Pro Cys Gln Gln Pro His Pro Ser Pro Cys Gln
            100                 105                 110 acc                                                                    339
Thr

<210> SEQ ID NO 4
<211> LENGTH: 113
<212> TYPE: PRT
<213> ORGANISM: Zea mays

<400> SEQUENCE: 4

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Val His Leu Pro Pro Pro Val His Leu
            35                  40                  45

Pro Pro Pro Val His Leu Pro Pro Val His Leu Pro Pro Val
        50                  55                  60

His Leu Pro Pro Pro Val His Val Pro Pro Val His Leu Pro Pro
65                  70                  75                  80

Pro Pro Cys His Tyr Pro Thr Gln Pro Arg Pro Gln Pro His Pro
                85                  90                  95

Gln Pro His Pro Cys Pro Cys Gln Gln Pro His Pro Ser Pro Cys Gln
            100                 105                 110

Thr

<210> SEQ ID NO 5
<211> LENGTH: 276
<212> TYPE: DNA
<213> ORGANISM: Zea mays
<220> FEATURE:
<221> NAME/KEY: CDS
<222> LOCATION: (1)..(276)
<223> OTHER INFORMATION:

<400> SEQUENCE: 5 atg agg gtg ttg ctc gtt gcc ctc gct ctc ctg gct ctc gct gcg agc     48
Met Arg Val Leu Leu Val Ala Leu Ala Leu Leu Ala Leu Ala Ala Ser
1               5                   10                  15 gcc acc tcc acg cat aca agc ggc ggc tgc ggc tgc cag cca ccg ccg     96
Ala Thr Ser Thr His Thr Ser Gly Gly Cys Gly Cys Gln Pro Pro Pro
            20                  25                  30 ccg gtt cat cta ccg ccg ccg gtg cat ctg cca cct ccg gtt cac ctg    144
Pro Val His Leu Pro Pro Pro Val His Leu Pro Pro Pro Val His Leu
            35                  40                  45 cca cct ccg gtg cat ctc cca ccg ccg gtc cac ctg ccg ccg ccg gtc    192
Pro Pro Pro Val His Leu Pro Pro Pro Val His Leu Pro Pro Pro Val
        50                  55                  60 cac ctg cca ccg ccg gtc cat gtg ccg ccg ccg gtt cat ctg ccg ccg    240
His Leu Pro Pro Pro Val His Val Pro Pro Pro Val His Leu Pro Pro
65                  70                  75                  80 cca cca tgc cac tac cct act caa ccg ccc cgg acc                    276
Pro Pro Cys His Tyr Pro Thr Gln Pro Pro Arg Thr
                85                  90

<210> SEQ ID NO 6
<211> LENGTH: 92
<212> TYPE: PRT
<213> ORGANISM: Zea mays
```

<400> SEQUENCE: 6

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
65                  70                  75                  80

Pro Pro Cys His Tyr Pro Thr Gln Pro Pro Arg Thr
                85                  90

<210> SEQ ID NO 7
<211> LENGTH: 213
<212> TYPE: DNA
<213> ORGANISM: Zea mays
<220> FEATURE:
<221> NAME/KEY: CDS
<222> LOCATION: (1)..(213)
<223> OTHER INFORMATION:

<400> SEQUENCE: 7

```
atg agg gtg ttg ctc gtt gcc ctc gct ctc ctg gct ctc gct gcg agc        48
Met Arg Val Leu Leu Val Ala Leu Ala Leu Leu Ala Leu Ala Ala Ser
1               5                   10                  15 gcc acc tcc acg cat aca agc ggc ggc tgc ggc tgc cag cca ccg ccg        96
Ala Thr Ser Thr His Thr Ser Gly Gly Cys Gly Cys Gln Pro Pro Pro
            20                  25                  30 ccg gtt cat ctg ccg ccg cca tgc cac tac cct aca caa ccg ccc          144
Pro Val His Leu Pro Pro Pro Cys His Tyr Pro Thr Gln Pro Pro
        35                  40                  45 cgg cct cag cct cat ccc cag cca cac cca tgc ccg tgc caa cag ccg       192
Arg Pro Gln Pro His Pro Gln Pro His Pro Cys Pro Cys Gln Gln Pro
    50                  55                  60 cat cca agc ccg tgc cag acc                                          213
His Pro Ser Pro Cys Gln Thr
65                  70
```

<210> SEQ ID NO 8
<211> LENGTH: 71
<212> TYPE: PRT
<213> ORGANISM: Zea mays

<400> SEQUENCE: 8

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Cys His Tyr Pro Thr Gln Pro Pro
        35                  40                  45

Arg Pro Gln Pro His Pro Gln Pro His Pro Cys Pro Cys Gln Gln Pro
    50                  55                  60

His Pro Ser Pro Cys Gln Thr
65                  70

<210> SEQ ID NO 9
<211> LENGTH: 180

```
<212> TYPE: DNA
<213> ORGANISM: Zea mays
<220> FEATURE:
<221> NAME/KEY: CDS
<222> LOCATION: (1)..(180)
<223> OTHER INFORMATION:

<400> SEQUENCE: 9 atg agg gtg ttg ctc gtt gcc ctc gct ctc ctg gct ctc gct gcg agc      48
Met Arg Val Leu Leu Val Ala Leu Ala Leu Leu Ala Leu Ala Ala Ser
1               5                   10                  15 gcc acc tcc acg cat aca agc ggc ggc tgc ggc tgc caa tgc cac tac      96
Ala Thr Ser Thr His Thr Ser Gly Gly Cys Gly Cys Gln Cys His Tyr
                20                  25                  30 cct act caa ccg ccc cgg cct cag cct cat ccc cag cca cac cca tgc     144
Pro Thr Gln Pro Pro Arg Pro Gln Pro His Pro Gln Pro His Pro Cys
            35                  40                  45 ccg tgc caa cag ccg cat cca agc ccg tgc cag acc                     180
Pro Cys Gln Gln Pro His Pro Ser Pro Cys Gln Thr
        50                  55                  60

<210> SEQ ID NO 10
<211> LENGTH: 60
<212> TYPE: PRT
<213> ORGANISM: Zea mays

<400> SEQUENCE: 10

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Cys His Tyr
                20                  25                  30

Pro Thr Gln Pro Pro Arg Pro Gln Pro His Pro Gln Pro His Pro Cys
            35                  40                  45

Pro Cys Gln Gln Pro His Pro Ser Pro Cys Gln Thr
        50                  55                  60

<210> SEQ ID NO 11
<211> LENGTH: 26
<212> TYPE: DNA
<213> ORGANISM: Artificial Sequence
<220> FEATURE:
<223> OTHER INFORMATION: Synthetic Construct

<400> SEQUENCE: 11
tcatgagggt gttgctcgtt gccctc                                         26

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
ccatggcgtg ggggacaccg ccggc                                          25

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
```

-continued

```
ccatggtctg gcacgggctt ggatgcgg                                          28

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
ccatggtccg gggcggttga gtagggta                                          28

<210> SEQ ID NO 15
<211> LENGTH: 122
<212> TYPE: DNA
<213> ORGANISM: Artificial Sequence
<220> FEATURE:
<223> OTHER INFORMATION: Synthetic Construct

<400> SEQUENCE: 15
catggacgac gacgacaagt gctccaacct ctctacctgc gttcttggta agctctctca       60
ggagcttcac aagctccaga cttaccctag aaccaacact ggttccggta ccctggttg       120 at                                                                     122

<210> SEQ ID NO 16
<211> LENGTH: 122
<212> TYPE: DNA
<213> ORGANISM: Artificial Sequence
<220> FEATURE:
<223> OTHER INFORMATION: Synthetic Construct

<400> SEQUENCE: 16
ctagatcaac caggggtacc ggaaccagtg ttggttctag ggtaagtctg gagcttgtga       60
agctcctgag agagcttacc aagaacgcag gtagagaggt tggagcactt gtcgtcgtcg      120
tc                                                                     122
```